(12) United States Patent
Siddiqui

(10) Patent No.: US 11,321,988 B2
(45) Date of Patent: May 3, 2022

(54) PROCESSING DEVICE FOR CURRENCY BILLS AND A METHOD OF USE THEREOF

(71) Applicant: Mahbub Alam Siddiqui, Honolulu, HI (US)

(72) Inventor: Mahbub Alam Siddiqui, Honolulu, HI (US)

(73) Assignee: AMRO-ASIAN TRADE, INC, Honolulu, HI (US)

( * ) Notice: Subject to any disclaimer, the term of this patent is extended or adjusted under 35 U.S.C. 154(b) by 0 days.

(21) Appl. No.: 17/525,911

(22) Filed: Nov. 14, 2021

(65) Prior Publication Data

US 2022/0076522 A1   Mar. 10, 2022

Related U.S. Application Data

(60) Provisional application No. 63/235,873, filed on Aug. 23, 2021.

(51) Int. Cl.
| | |
|---|---|
| *G07D 11/50* | (2019.01) |
| *G07D 11/18* | (2019.01) |
| *A61L 2/10* | (2006.01) |

(52) U.S. Cl.
CPC .............. *G07D 11/50* (2019.01); *A61L 2/10* (2013.01); *G07D 11/18* (2019.01); *A61L 2202/11* (2013.01); *A61L 2202/122* (2013.01); *A61L 2202/14* (2013.01); *A61L 2202/26* (2013.01); *G07D 2211/00* (2013.01)

(58) Field of Classification Search
CPC ..... A61L 2/08; A61L 2/10; A61L 2/12; A61L 2202/11; A61L 2202/122; A61L 2202/14; A61L 2202/26; G07D 11/50; G07D 11/18
See application file for complete search history.

(56) References Cited

U.S. PATENT DOCUMENTS

| | | | |
|---|---|---|---|
| 9,498,551 B2 * | 11/2016 | Yanke | ........................ A61L 2/18 |
| 2005/0053183 A1 * | 3/2005 | Abe | ........................ G07D 7/121 |
| | | | 377/94 |

* cited by examiner

*Primary Examiner* — Timothy C Cleveland
(74) *Attorney, Agent, or Firm* — Barry Choobin; Patent 360

(57) ABSTRACT

A currency bill processing device for counting, denominating, discriminating, and/or sorting the currency bills and subsequently disinfecting the currency bills without any manual intervention. The currency bill processing device can process the currency bills at a speed of up to 1000 bills per minute. The currency bill processing device includes one or more elongated UV-C LED strips mounted on a rigid aluminum or copper base which can be mounted on an outer or exposed side of a support plate or reject receptacle plate or stacker guide bar plate located at the end of the currency bill conveying path. A disinfection unit of the currency bill processing device including the elongated UV-C LED strip that can activate and deactivate with turning-on and -off of the currency bill conveying mechanism respectively.

20 Claims, 34 Drawing Sheets

PROCESSING DEVICE FOR CURRENCY BILLS AND A METHOD OF USE THEREOF

CROSS-REFERENCE TO RELATED APPLICATIONS

This application claims priority from the U.S. provisional patent application Ser. No. 63/235,873, filed on Aug. 23, 2021, which is incorporated herein by reference in its entirety.

FIELD OF INVENTION

The present invention relates to a processing device for currency bills, more particularly, the present invention relates to a processing device that can count, discriminate and/or sort the currency bills and simultaneously can disinfect the currency bills using sterilizing radiation.

BACKGROUND

Contagious diseases are diseases that can spread from an infected person to a healthy person by the transmission of the pathogen causing the infection. A pathogen can spread from one person to another in a variety of ways, such as by air, food, and surface. The spread of pathogens through surfaces is common. Typically, an infected person when touching a surface can transmit the pathogen to the surface. The pathogens can survive on the surface for variable duration. When a healthy person comes in contact with the surface, the pathogens from the surface can be transmitted to the healthy person.

Certain pathogens can quickly spread from one person to another and can result in epidemics and pandemics. SARS Covid-19 infection is an extremely contagious viral pathogen. World health organization declared covid-19 as a pandemic in March 2020. Such endemic and pandemics have been responsible for the death of millions throughout history.

Currency bills are quickly exchanged among many and come in direct contact with hands, and thus are a common surface for the spread of pathogens. The rough surface of the currency bills provides a good niche for microorganisms and other particulates to settle and accumulate over the long term and thereby constitute a potential source of infection. As paper money offers an attractive window into human-driven microbial community diversity due to the high frequency of manual currency exchange in commerce, food service, and travel activities that are likely to influence the types of organisms present. The levels and diversity of microbial contamination of currency bills depend on a number of factors including the period of their circulation, handling, and texture. The capacity of currency bills to absorb moisture also facilitates the growth and viability of microorganisms.

Thus, a need is appreciated for a device that can sterilize the currency notes in circulation from time to time.

The term "currency bill" hereinafter refers to currency bills issued by a U.S. governmental agency as a legal tender or any other non-US agency and includes substitute currency media. The US legal tender can include paper money. The substitute currency media can include any physical medium that is exchanged between persons and has a monetary value, such as the bank checks issued by financial institutions, casino scripts and casino tickets issued by casinos, vouchers and coupons, and certificates issued by entities that utilize barcoded transaction records.

The term disinfection hereinafter refers to partially or completely killing or inactivation of microorganisms on a surface of the currency bill.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a currency processing device for disinfecting the currency bills.

It is another object of the present invention that the currency processing device can count the currency bills.

It is another object of the present invention that the currency processing device can discriminate and sort the currency bills.

It is still another object of the present invention that the currency processing device can disinfect a large number of currency bills in a short duration.

It is yet another object of the present invention that the currency processing device does not expose nearby persons to sterilizing radiation.

It is a further object of the present invention that the currency bills can be disinfected automatically without any intervention from the operator for disinfecting the currency bills.

It is still an additional object of the present invention that a disinfecting unit can retrofit to a known currency bill counting and/or discrimination device.

It is also an object of the invention to mount or install at least one of the rigid and exposed UV-C LED strip on the outer (rear) side of the support plate or reject output receptacle plate or underneath of stacker guide bar plate located about stacker output receptacle plate and when this germicidal UV-C LED strip element is mounted or installed on them on their outer (rear) side and installed into the devices, this outer (rear) side of the plate with the germicidal UV-C LED strip element installed on it, face the passing currency bills or media that are conveying at a high-speed underneath them and receiving UV-C radiation at a frequency of about 269 nm at their peak on them downwardly on the face and rear of the currency bills and currency media passing under and being sterilized and disinfected in the process, at least reducing or eliminating all known germs that may inhabit and accumulated on the surface of currency bills.

In one aspect, disclosed is a currency processing device for currency bills that can count and/or discriminate the currency bills and simultaneously can also provide for disinfecting the currency bills using sterilizing radiation, such as UV-C radiation. The disclosed currency processing device can incorporate features of known currency bill counting and/or discriminating devices and includes a disinfecting unit underneath (outer side) of a reject plate or support plate or a stacker guide plate. In one case, the disinfecting unit can include an array of UV-C LEDs positioned to irradiate the currency bills in the currency processing device.

In one aspect, the disinfecting unit and the motor of the currency processing device can be operably coupled to a control unit. The motor can provide for running the components of the currency processing device for counting and/or discriminating the currency bills.

In one aspect, the disclosed currency processing device can include a bill input station for placing a stack of up to a few hundreds of currency bills; optionally a plurality of output receptacles; a currency bill recognition unit utilizing optical scanning means to recognize, denominate, discriminate, sort, and/or count the currency bills; authentication unit to check for the suspect; a conveying mechanism to convey the currency bills at a high-speed and then divert currency bills to single stacker output receptacle or multiple output receptacles after being successfully recognized and denominated for currency bills based on the judgment made by the currency recognition unit. Currency denominating and sorting devices can also include a reject output receptacle to receive currency bills or currency media that cannot be recognized. Alternatively, the disclosed devices may not include any reject pocket and all processed bills are conveyed to the only stacker pocket with a halting system when a currency bill is not recognized, or media decided successfully.

In one aspect, the disclosed currency bill processing device can be compact and can be placed at a desk or at a back counter or at a cash register counter, or at the back office. The disclosed device can be used in banks and similar commercial establishments as a substitute to regular currency counting and discriminating device. Additionally, the disclosed device can also be used at point-of-sale desks, wherein the disclosed currency bill processing device can be made available in a range of sizes and functionality but includes at least one major function of disinfecting the currency bills, and more particularly a large number of currency bills can be counted and/or discriminated and disinfected at a high rate.

In one aspect, the disinfecting unit can include a UV-C LED strip of about 7 inches in length and about 0.5 inches in width, and the UV-C LED strip can include at least 8 units of LEDs that can generate radiation in a range of about 260-280 nm wavelength. The disclosed UV-C LED strip can irradiate the surface of the passing currency bills at a high speed. The currency bills can be partially or fully disinfected using the sterilizing ultraviolet radiation or similar sterilizing radiation just after currency bills are denominating/counted/sorted and before delivering to the public or put into circulation.

In one aspect, the disinfecting unit including the UV-C LED strip can be installed in the currency bill processing device underneath (outside side) of a reject plate or support plate or stacker guide bar plate located above stacker output receptacle(s) where the currency bills are delivered to after being counted and/or denominated, wherein the at least one UV-C LED strip can remain virtually hidden from operator's eyes, require no operator's intervention to operate and effective in at least partially or completely disinfecting the passing currency bills.

In one aspect, the operation of the disinfecting unit can be automated and coupled to the motor of the disclosed currency counting device. The motor and the disinfecting unit both can be powered by a common energy source and the operation of the motor can automatically turn on the disinfecting unit and similarly, the disinfecting unit can be turned off.

In one aspect, the currency bills passing underneath of the UV-C LEDs of the disinfecting unit can be in close proximity of about 1 cm distance and at a rate up to about 1000 bills per minute, and means can be provided to prevent any kind of contact of the currency bills with the disinfecting unit, thus avoiding any kind of damage to UV-C LEDs while still able to at least partially or completely disinfect the currency bills during the process prior they are delivered to the output stacker/station ready for tellers to remove and handed over to their customers or place them in a vault for later circulation to the general public.

In one aspect, disclosed is a desk type compact currency bill discriminating, denominating, and sorting device that can disinfect the currency bills at a high speed after denominating, discriminating, or decoding them, and finally deliver the disinfected currency bills to their respective output receptacles judged and determined by a currency recognition unit.

In one aspect, UV-C LED strip can be rigid and mounted to a location completely outside of the currency bills conveying mechanism, particularly outside of the complex and fast-moving currency bills convey path and separate from various complex scanning and detection sensors and their mechanical components or fast-moving feeding and conveying mechanism of the currency denominating and sorting devices so not to interrupt the intended functionality, operation and performance of the currency denominating and sorting devices.

In one aspect, the currency bills can be disinfected simultaneous to counting and/or discriminating the currency bill and no separate effort may be needed on part of the operator to turn the disinfecting unit on and off.

In one aspect, the length of the UV-C LED strip can be proportional to the length of the currency bill. Preferably, the UV-C LED strip can be thin so that enough space can be maintained between the currency bill and the UV-C LED strip avoiding any jamming issue and damage to the UV-C LEDs.

In one aspect, the disinfecting unit can include a UV-C LED strip with a rigid aluminum or copper base having at least 7 inches in length and at least 0.5 inches in width. The UV-C LED strip can include at least eight UV-C LEDs literary arranged in one or more rows. The disinfecting unit can further include circuitry electrically coupled to at least 8 UV-C LEDs.

In one aspect, disclosed is a currency bill processing device that can disinfect the currency bill in circulation at the time of counting and/or discriminating the currency bill. While passing to the respective output receptacles, the currency bills pass through underneath of UV-C LED strip, wherein the UV-C LED strips are exposed and are encased in a container or in a container with a lens. When currency bills pass underneath of this rigid germicidal UV-C LED strip within about 1 cm distance far apart at high-speed up to 1000 bills per minute, the currency bills are radiated by the UV-C LEDs at a frequency of about 269 nm at its peak downwardly from the top covering the front and rear side of the currency bills disinfecting the currency bills prior reaching their designated stacker output receptacles.

In one aspect, the currency bill processing device can be implemented as different currency bills processing devices, such as bill validators, currency dispensing and recycling devices, ATMs, currency bills or casino tickets redemption machines, or similar devices used in cash processing industries and in casinos.

In one aspect, the disinfection unit and other components of the currency bill processing device for counting and/or discriminating the currency bills can be powered by a common power supply.

In one aspect, the operating of the disinfecting unit can be controlled to increase efficiency, minimize waste, and increase the life of the UV-C LEDs. In one aspect, the disinfecting unit can be operably coupled to the conveying mechanism responsible for moving the currency bills through a relay, such as the activation of the motor for moving the currency bills can automatically energize the relay sending a signal to disinfecting unit. When the motor turns off or is not moving the currency bills, the relay may get de-energized which in turn sends a signal to the disinfecting unit to turn off or standby.

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

FIG. 4ba shows another exemplary embodiment of the currency bill processing device having two parallel units of UV-C LED strips installed on the outer (opposite) side of the reject output receptacle, according to an exemplary embodiment of the present invention.

FIG. 4ca is still another front perspective view of the currency bill processing device shown in FIG. 4ba, according to an exemplary embodiment of the present invention.

FIG. 4da is a bottom perspective view of the currency bill processing device shown in FIG. 4ba, according to an exemplary embodiment of the present invention

FIG. 7ba is an electrical diagram of the currency bill processing device having two UV-C LED strips, according to an exemplary embodiment of the present invention.

DETAILED DESCRIPTION

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

Disclosed is a currency bills processing device that can count, discriminate, denominate, and/or sort the currency bills and also can provide for disinfection of the processed currency bills. The disclosed currency bills processing device includes a disinfection unit that can irradiate the currency bills with sterilizing radiation, such as the radiation in the UV-C spectrum. The disinfecting device can also be retrofit into an existing currency counter, discriminator, denominator, and/or sorter. The disinfection unit can include at least one UV-C LED strip that can be installed proximate to the passing currency bills in the currency bills processing device. Preferably, the disinfection unit can be installed at an end of the conveying mechanism and other movable parts of the currency bills processing device. The motor for the conveying mechanism for conveying the currency bill generally works at a high-speed processing hundreds of currency bills per minute. The disinfection unit can match the speed of the conveying mechanism for disinfecting the currency bills. In one implementation, the disinfecting unit can disinfect the currency bills at a speed of about 1000 bills per minute.

To effectively reduce the microbial load settled in or accumulated over a long period on the surface of the currency bills, the UV-C LED strip can be installed towards the end conveying path emitting UV-C radiation downwardly towards the passing currency bills. The UV-C LED strip can be positioned such as to effectively irradiate the passing currency bill while the UV-C radiation either directly or reflected does not reach outside the currency bills processing device. The disclosed currency bills processing device is safe, and the operator of the currency bills processing device is not exposed to any UV radiation. Moreover, there is no need for encasing the UV-C LED irradiation zone in a container or similar casing, but the UV-C LED strip may be exposed within the currency bills processing device. Preferably, the length of the UV-C LED strip can be equal to or more than the length of the currency bill.

Figure 1:
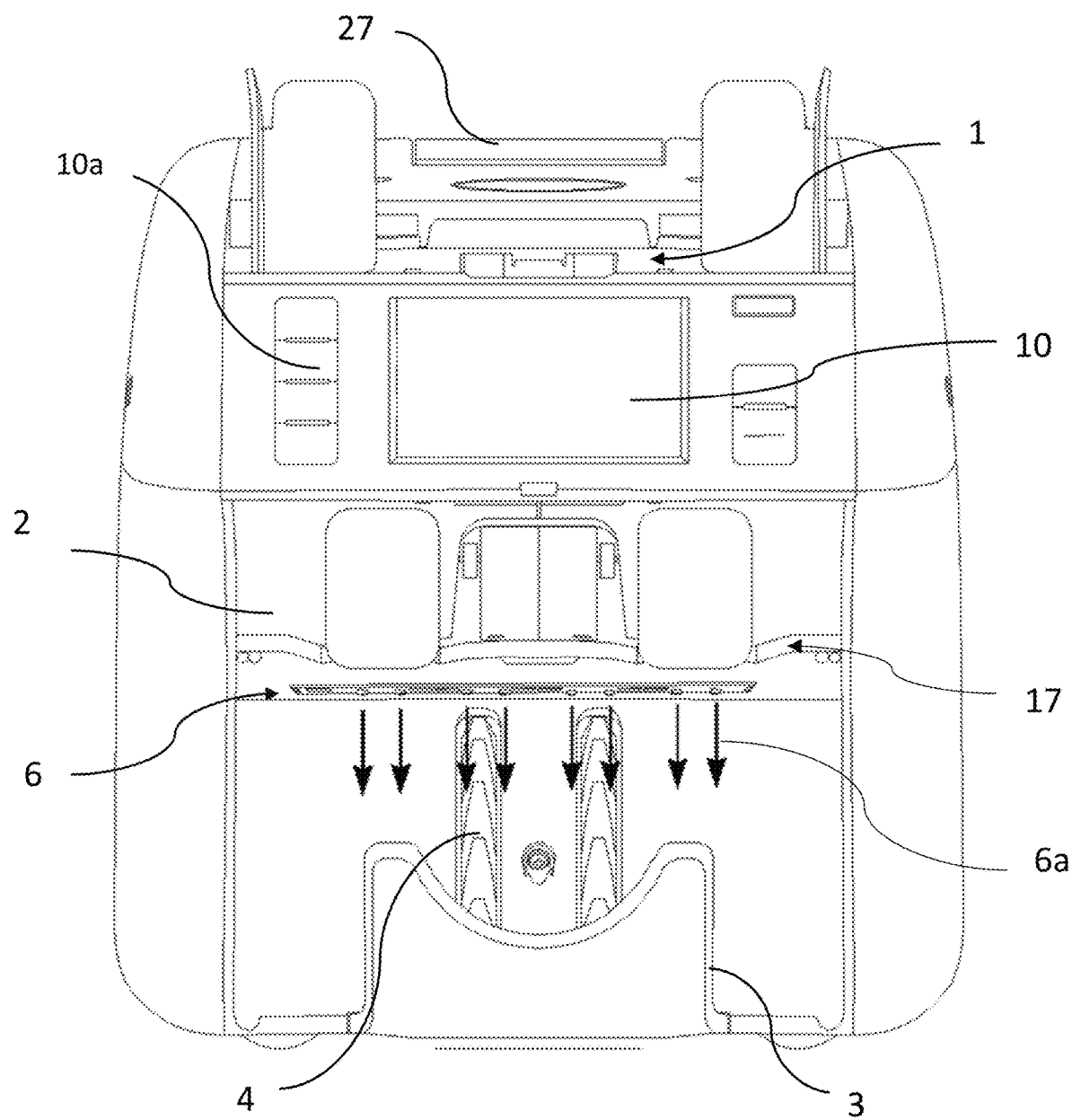
FIG. 1 is a perspective view of a currency bill processing device that can be at a desk of teller counter at a bank or other financial or retails or casinos, having a single stacker output receptacle and a reject output receptacle installed with a disinfecting unit, according to an exemplary embodiment of the present invention.
Figure 2:
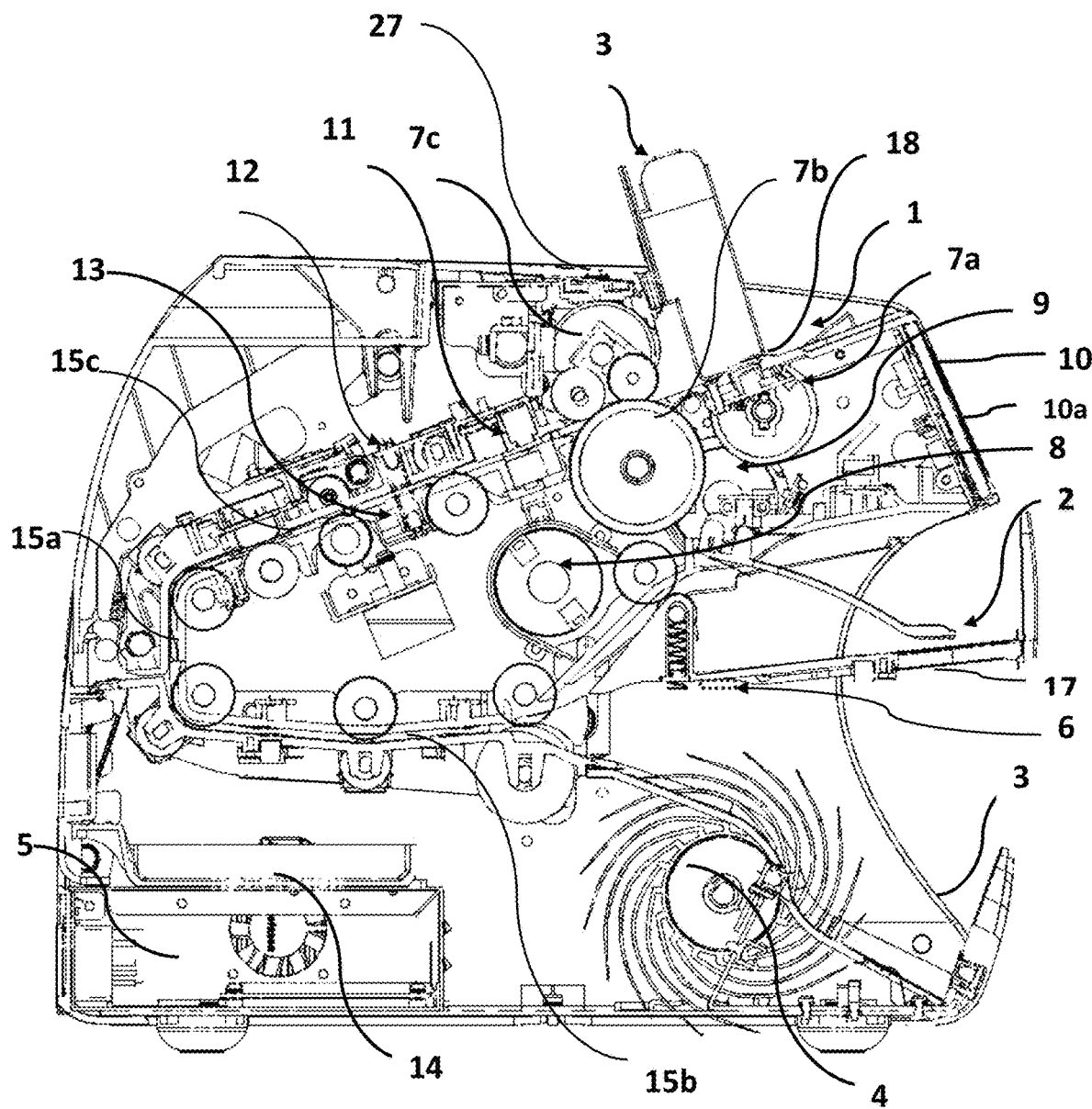
FIG. 2 is a cross-sectional of the currency bill processing device as in FIG. 1 shows UV-C LED strip installed on an outer (opposite) side of a reject output plate facing passing currency bills, according to an exemplary embodiment of the present invention.

Referring to FIGS. 1 and 2, there is shown the disclosed currency bills processing device 27. The currency bills processing device 27 can be of a standard dimension, for example, the dimensions can be about 13.3 inches in width, 13.8 inches in length, and 14.4 inches in height. The currency bills processing device 27 can include a disinfection unit containing a UV-C LED strip 6 that can irradiate the currency bills, the direction of the UV-C radiation is shown by arrows 6a. An exemplary embodiment of the disinfecting unit 6b is shown in FIG. 7b. As can be seen in FIGS. 1 and 2, the UV-C LED strip is exposed and not encased in a container or similar encasing. The currency bills processing device 27 can include a bill input station or receptacle or bill input station 1 where a stack of currency bills that need to be discriminated, recognized, and counted can be placed. The currency bills in the bill input receptacle 1 are acted upon by a bill sensor 18 (not shown) to sense that there is an object placed on the bill input station 1 and once sensed, the currency bills start to feed and conveyed using a combination of feed rollers 7a, 7b, 7c (FIG. 2) and feed motor 9 (FIG. 2) one bill at a time with the narrow dimension of the bills being parallel to the bill input station 1. Currency bills then pass the currency recognition unit 11 (FIG. 2) and authentication unit 19 (FIG. 5) consisting of several authentication detector/sensor, such as ultraviolet light 12 and magneto-resistive (MR) sensor 13 (FIG. 3) where the currency bill can be recognized, denomination of the bill can be identified and discriminated, suspect detection checking may also be performed, and in case of currency media such as casino tickets, they can be decoded by printed barcode or in the case of banknote MICR (magnetic ink character recognition). It is well-known in the art that substitutes currency media are not subject to this authentication checking due to characteristics of currency media. Once judgment is made by the currency bill recognition unit as to the denomination and value of the currency bills or currency media are properly recognized, read, and decoded, then currency bills and currency media then conveyed forward using the conveying mechanism at a speed up to about 1000 bills per minute via bill conveying path 15a, 15b, 15c (FIG. 2).

The conveying mechanism usually consists of many small rollers and shafts to drive currency bills at a high speed from input to output. The structure and functioning of the conveying mechanism in currency counters, discriminators, and like are known in the art and not described herein in detail. The next step would be for currency bills to pass through a disinfection zone created by the disinfecting unit. The disinfection zone can be irradiated by a strip of UV-C LEDs 6, wherein the currency bills can be disinfected prior to delivering to a single or plurality of stacker output receptacles 3 based on the judgment made by the currency recognition unit 11 (FIG. 2). The main stacker output receptacle is equipped with a pair of stacker wheel 4 for stacking currency bills or currency media in alignment. In one case, if the passing currency bills could not be recognized, the unrecognized currency bills can be diverted to a reject output receptacle 2 (FIG. 1). As described below, alternative device 29 (FIG. 15) includes more than one stacker output receptacle and would operate under the same principle.

Figure 5:
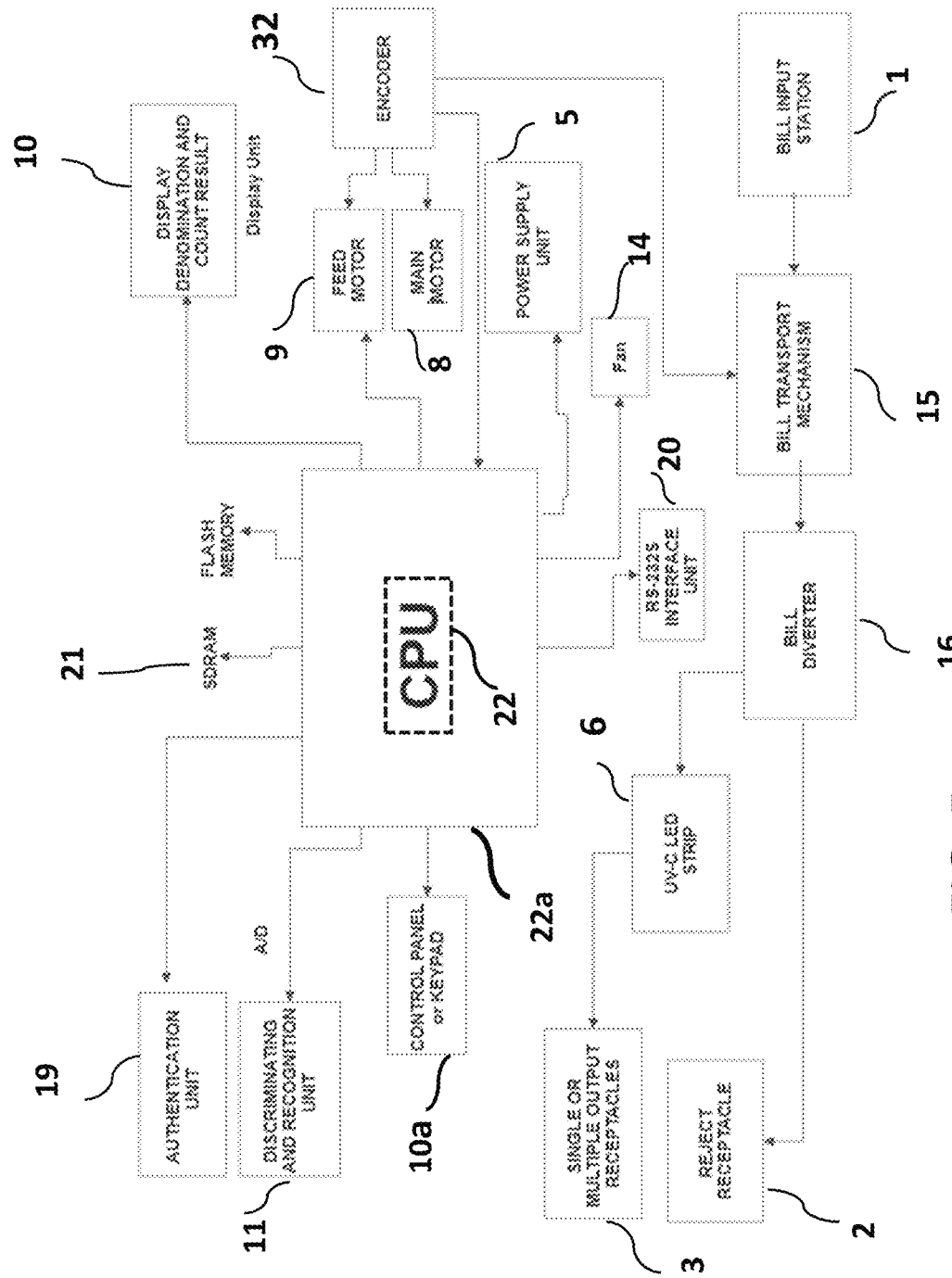
FIG. 5 is a functional block diagram of the currency bill processing device, according to an exemplary embodiment of the present invention.

One skilled in the art of currency processing devices would understand that currency denominating and sorting devices include a CPU 22 (FIG. 5) which is programmed to count the number of currency bills, denominating recognized currency bills, and determine the cumulative total of the currency amount represented by the currency bills scanned through currency recognition unit 11. The CPU 22 (FIG. 5) is also linked to a control panel consisting of buttons or keypads or simply touch keys 10a for selection of various functionality and operation of the device and include a touch screen or LCD display unit 10 (FIG. 1. and FIG. 5) which is adapted to provide a display of the number of bills counted, the breakdown of the bills and currency denomination, and the cumulative total of the currency value represented by counted bills. The display unit 10 can also be adapted to provide a print-out of the displayed information in the desired format. CPU 22 (FIG. 5) also connected to RS232 interface ports 20 (FIG. 5) to connect to printer and external display unit and so (not shown here) to show the count and break-down of count as it displayed. As to Currency media, after successfully reading and decoding the currency recognition unit 11 and processed by CPU 22 and EPROM 20 (FIG. 5), results may display on the display unit 10 or to a printer connected to it or transfer results to a PC software connected via RS232 interface port 20 (FIG. 5).

Figure 3:
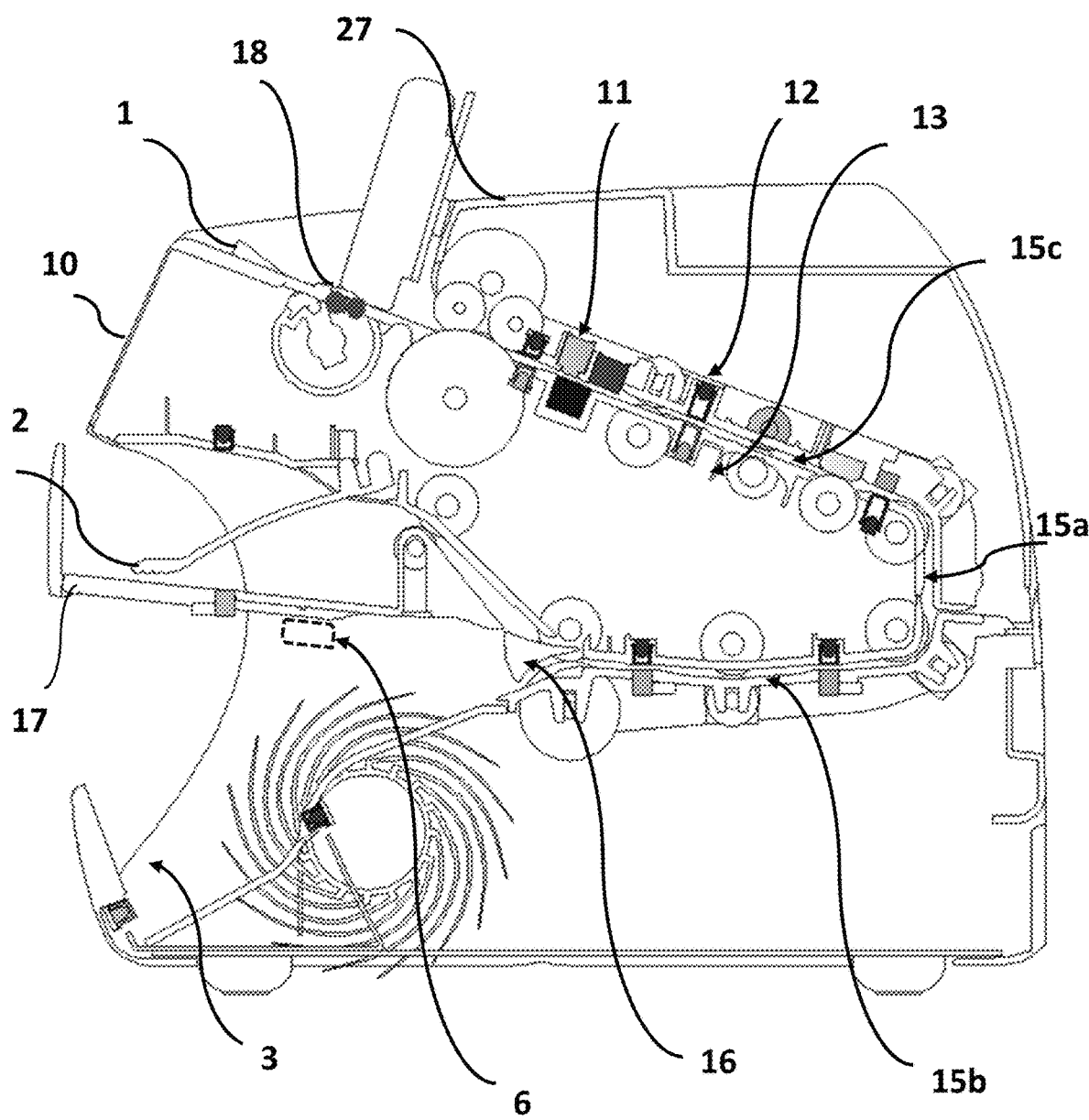
FIG. 3 is a side cross-sectional view of the currency bill processing device as in FIG. 1 illustrating currency bill conveying path, currency bill recognition unit, and an authenticating unit, according to an exemplary embodiment of the present invention.

Referring to FIG. 3. is an exploded internal perspective view of currency bills processing device 27 of FIG. 1 further showing the UV-C LED strip 6 exposed without having embedded in a container or in a container with the lens or in the enclosure of any kind. As described in detail under FIGS. 1 and 2, currency bills are fed using a combination of feed roller 7a, 7b, 7c, and feed motor 9 and passing through currency recognition unit 11 and authentication unit such as ultraviolet light 12 and magneto-resistive (MR) sensor 13 and then, conveyed through one bill at a time with the narrow dimension of the currency bill being parallel to the bill input station 1 and currency recognition unit 11 with the help of a conveying mechanism consisted of many rollers and shaft (shown on FIG. 3, but not explained here in details) and conveyed by the main motor 8 onto the currency bill conveying path 15a, 15b, 15c (FIG. 3). Towards the end of the bill conveying path, currency bills are diverted using a bill diverter 16 (FIG. 3) either to the reject output receptacle 2 or the single or multiple stacker output receptacle 3 (FIG. 5) depending on the judgment made by the currency recognition unit 11 and authenticating units 11 and 13. Currency bills that are not recognized or discriminated or denominated successfully by the currency recognition unit 11 may not be exposed to the UV-C irradiation, however, by nature of such currency denominating and sorting devices and operation wise, users usually re-run the currency bills through the device and a second scan may provide a better chance of being recognized and the previously rejected currency bills can be exposed to the UV-C LED strip 6 for disinfection. FIG. 3 also illustrates power supply unit 5 to supply current to both the feed and main motors 9 and 8 (FIGS. 2 and 5), currency recognition unit 11, authentication detectors/sensors 12 and 13 and the exposed UV-C LED strip 6 of the present invention.

Referring now to FIGS. 4a, 4b, 4c, 4d are perspective views of the same embodiment of device 27 of FIG. 1 illustrate one element of the embodiment of the present invention, more particularly the location of the present invention of at least one UV-C LED strip 6 which is exposed without any need for embedding in a container or in a container with a lens or in an enclosure of any kind to be installed on the embodiment of the currency denominating and sorting device 27 of the present invention.

Figure 4A:
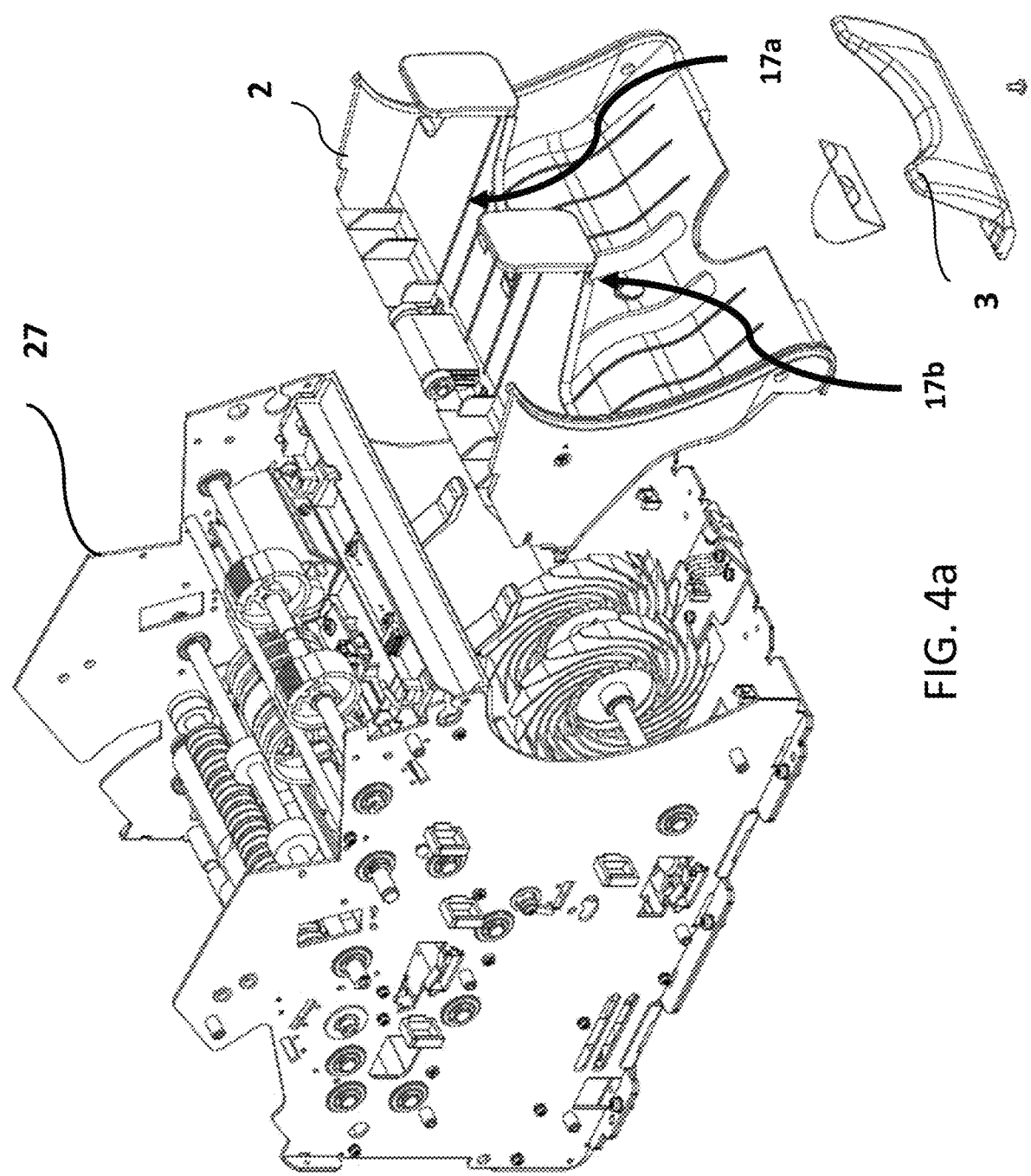
FIG. 4a is a perspective view of a reject output receptacle of the currency bill processing device shown in FIG. 1 and illustrating a top view (inner side) of a reject plate and a rigid UV-C LED strip installed on the outer side (opposite side) of the reject plate, according to an exemplary embodiment of the present invention.

FIG. 4a shows a separated reject output receptacle 2 of currency bills processing device 27. The reject output receptacle 2 consists of a plate having an inner side (front side) 17a where currency bills that are rejected for reasons such as for not being recognized or discriminated or read using the currency recognition unit 11 are delivered to prior to removal by the users. The reject receptacle 2 has an outer side (rear/opposite side) 17b over which the UV-C LED strip 6 can be mounted.

Figure 4B:
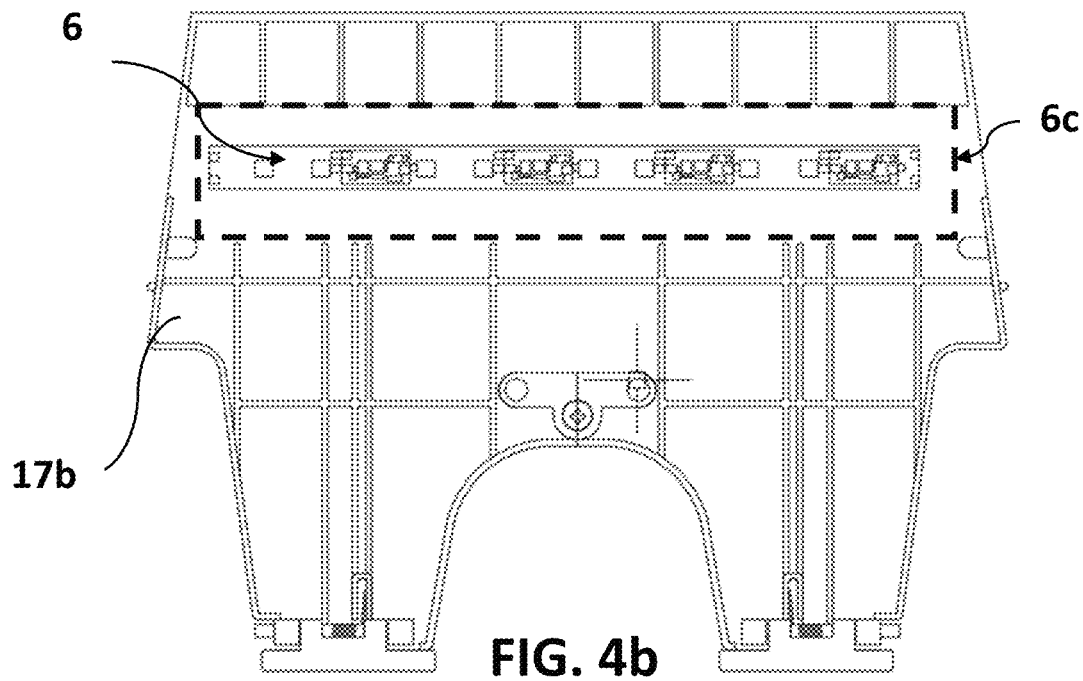
FIG. 4b is an outer (rear)-side perspective view of the reject output receptacle of the currency bill processing device shown in FIG. 1, according to an exemplary embodiment of the present invention.
Figure 4B:
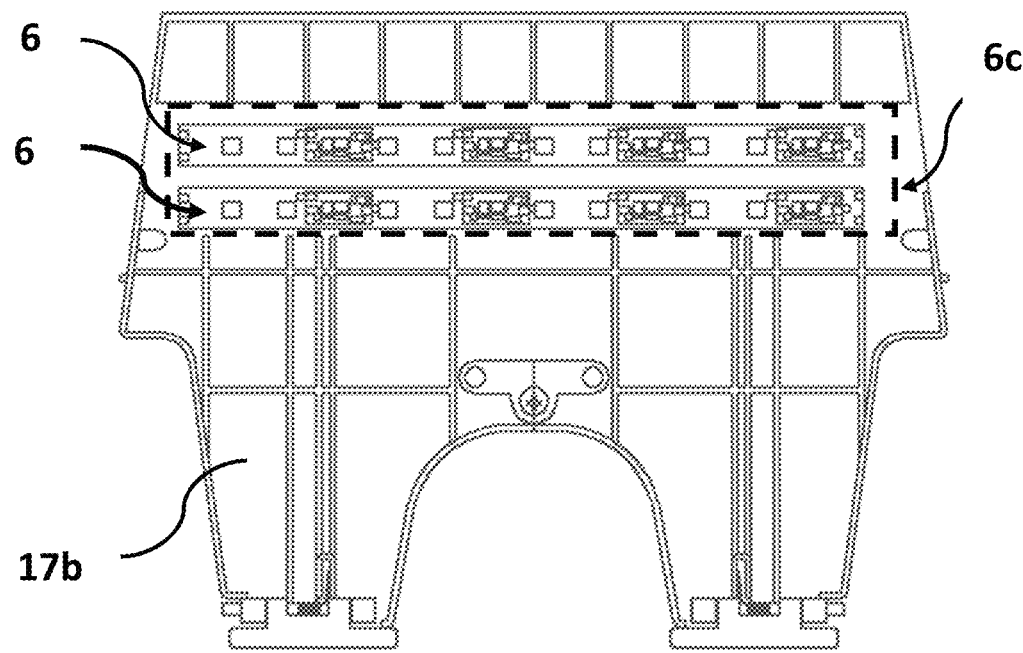

FIG. 4b is a perspective view of the outer/rear side 17b of the plate of the reject output receptacle 2 (FIG. 4a) further illustrating that the outer/rear side 17b has sufficient flat or smooth surface for the UV-C LED strip 6 while the UV-C LED strip 6 is exposed without any need for encasing the UV-C LED strip 6 in a container or enclosure of any kind, and conveniently. The outer/rear side 17b of the plate of reject output receptacle 2 (FIG. 4a) can be about at least 7.5 inches in length and about 6 inches in width and having at least about 7.5 inches length and 4 inches width smooth surface area 6c provide sufficient and appropriate space to accommodate at least two rigid UV-C LED strip 6, and the UV strip can be about 7 inches in length and 0.5 inches in width itself. The dimension of this plate of the reject output receptacle 2 of the currency denominating and sorting device 22 must be such as it is longer in length to accommodate the rigid UV-C LED strip 6 elements of the present invention and longer in length than a typical dimension of US currency bills, which is about 6.14 inches length and the casino tickets are about 6.3 inches long so that the UV-C LED strip 6 can cover the entire length of the currency bills for partially or complete disinfection.

FIG. 4ba is another perspective view of the outer side/rear side 17b of the plate of reject output receptacle 2 as described in detail in relates to FIG. 4b further illustrating two units the UV-C LED strip 6 installed conveniently. The outer side/rear side 17b of the plate of reject output receptacle 2 (FIG. 4a) is about 7.5 inches in length and 6 inches in width with having at least about 7.5 in length and 4 inches with a wide smooth surface area 6c provide sufficient and appropriate space to accommodate two units of the UV-C LED strip 6 which can be about 7 inches in length and 0.5 inches in width.

Figure 4C:
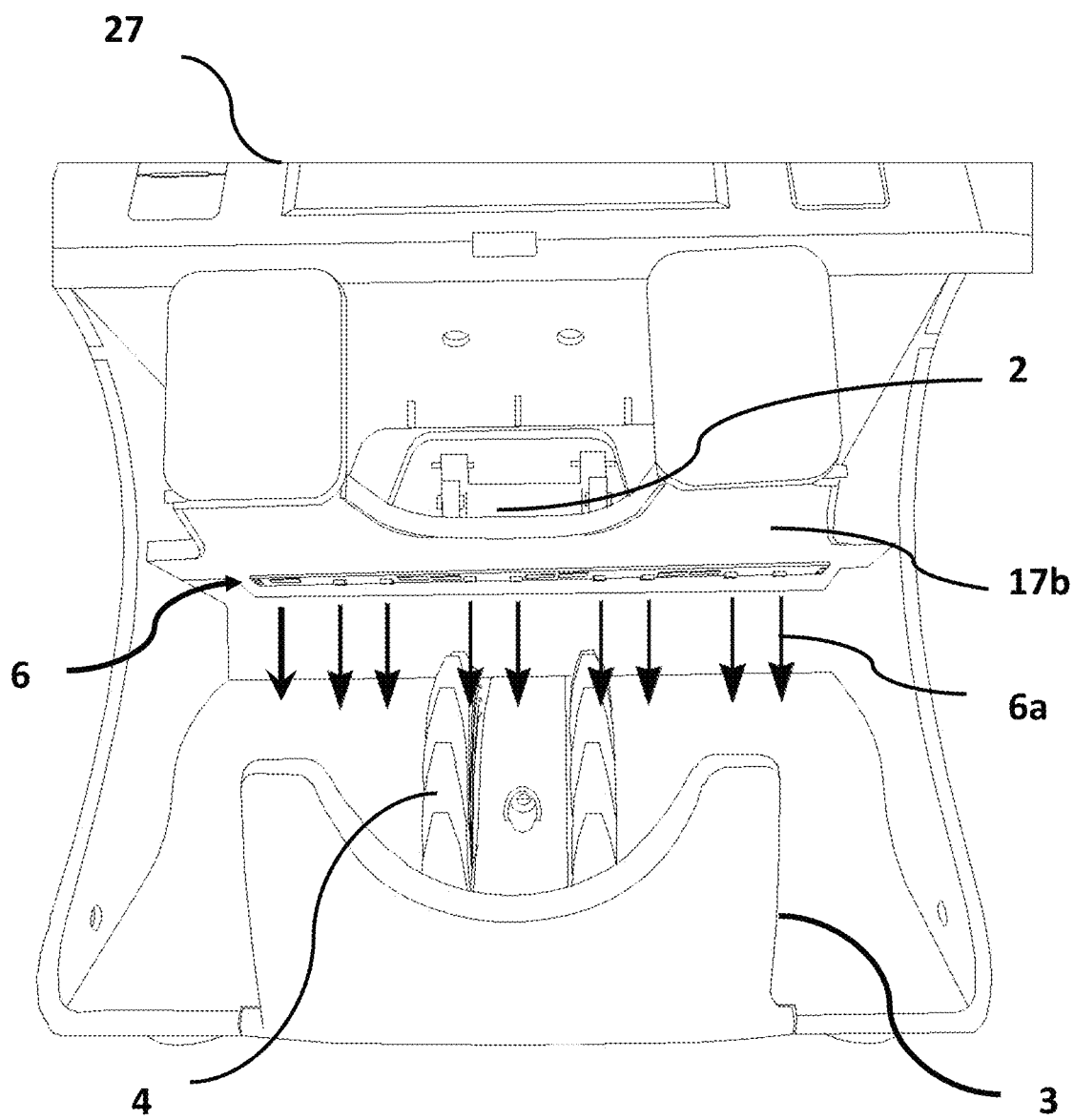
FIG. 4c is another front perspective view of the currency bill processing device shown in FIG. 1, according to an exemplary embodiment of the present invention.
Figure 4C:
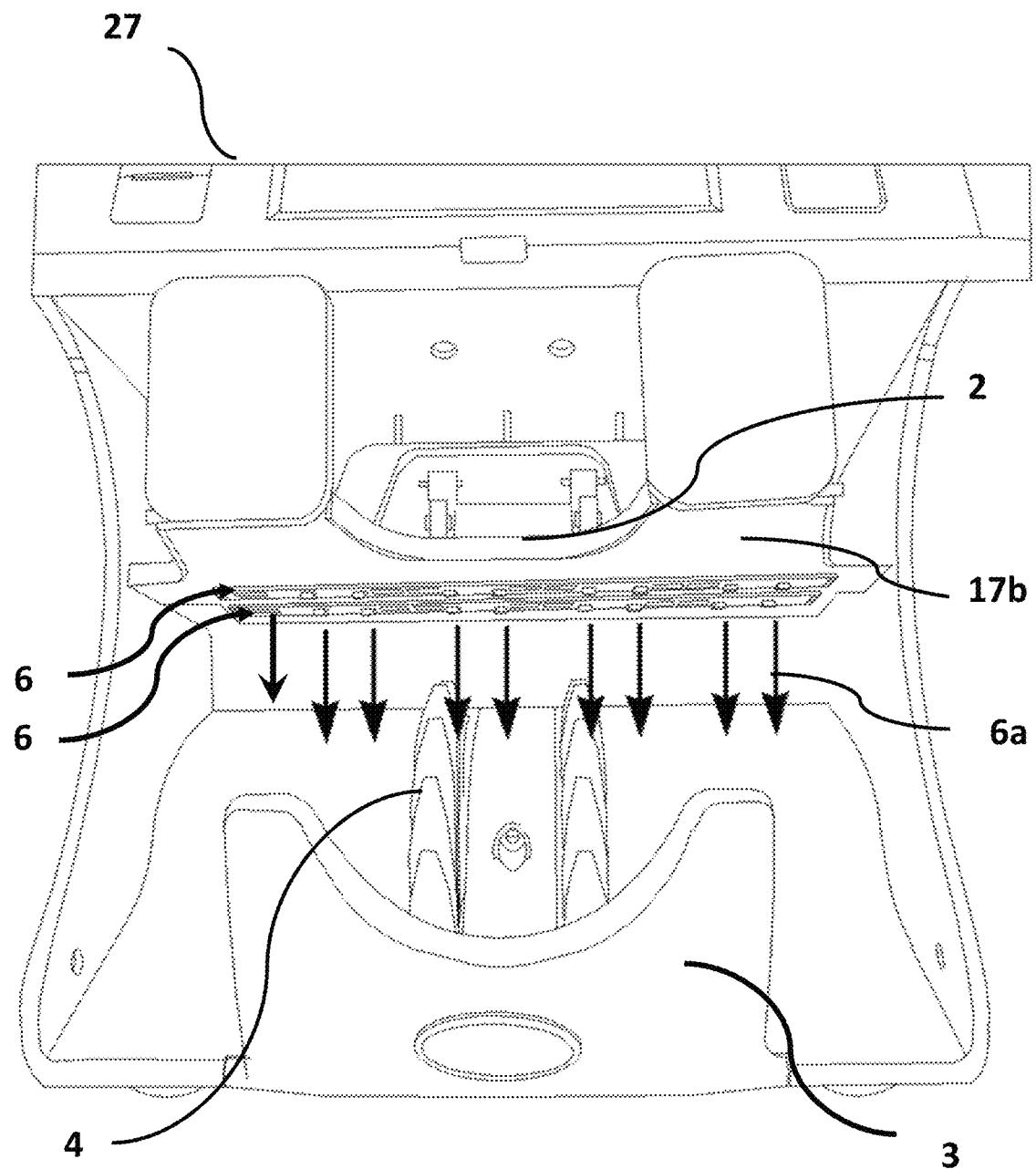
Figure 4D:
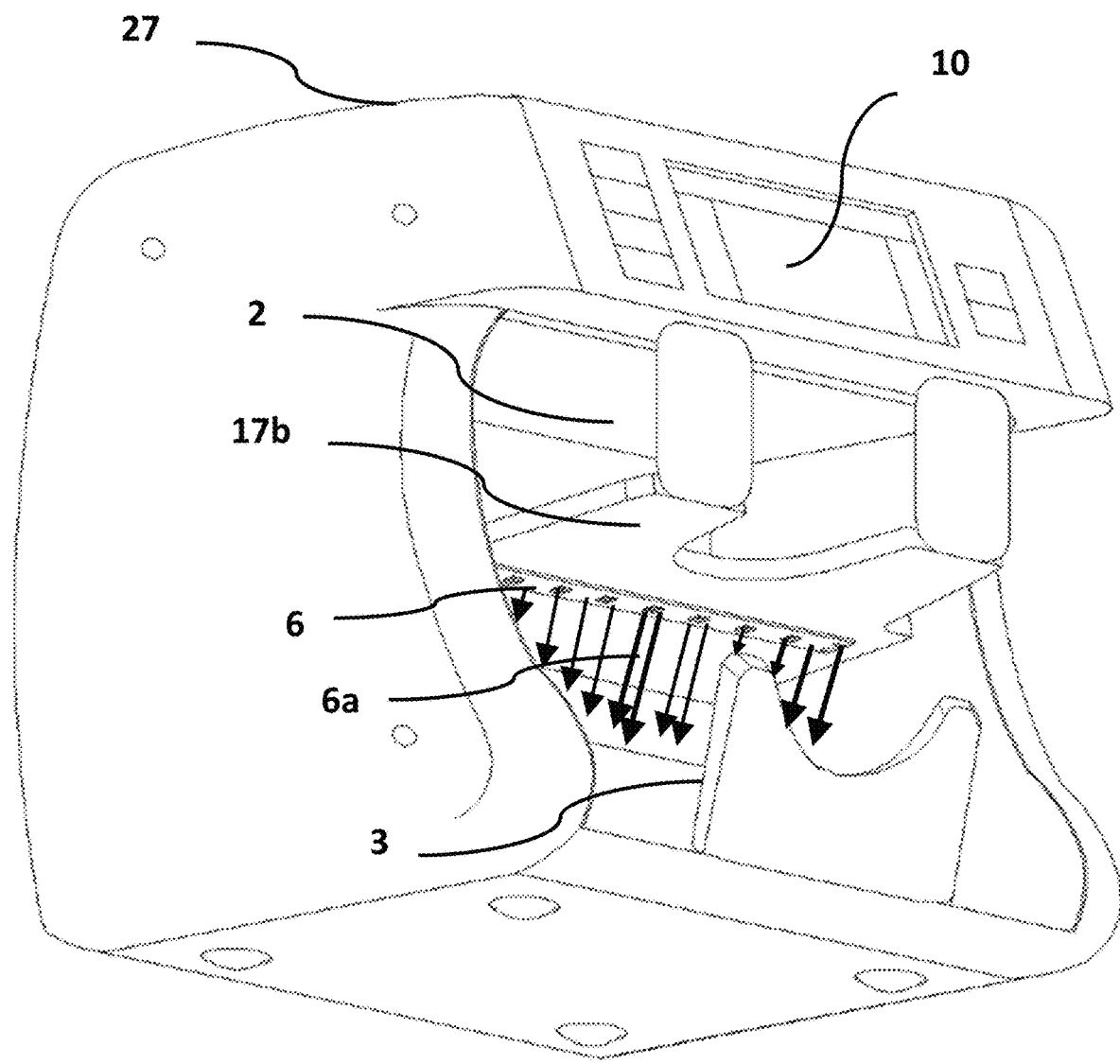
FIG. 4d is a bottom perspective view of the currency bill processing device shown in FIG. 1, according to an exemplary embodiment of the present invention.
Figure 4D:
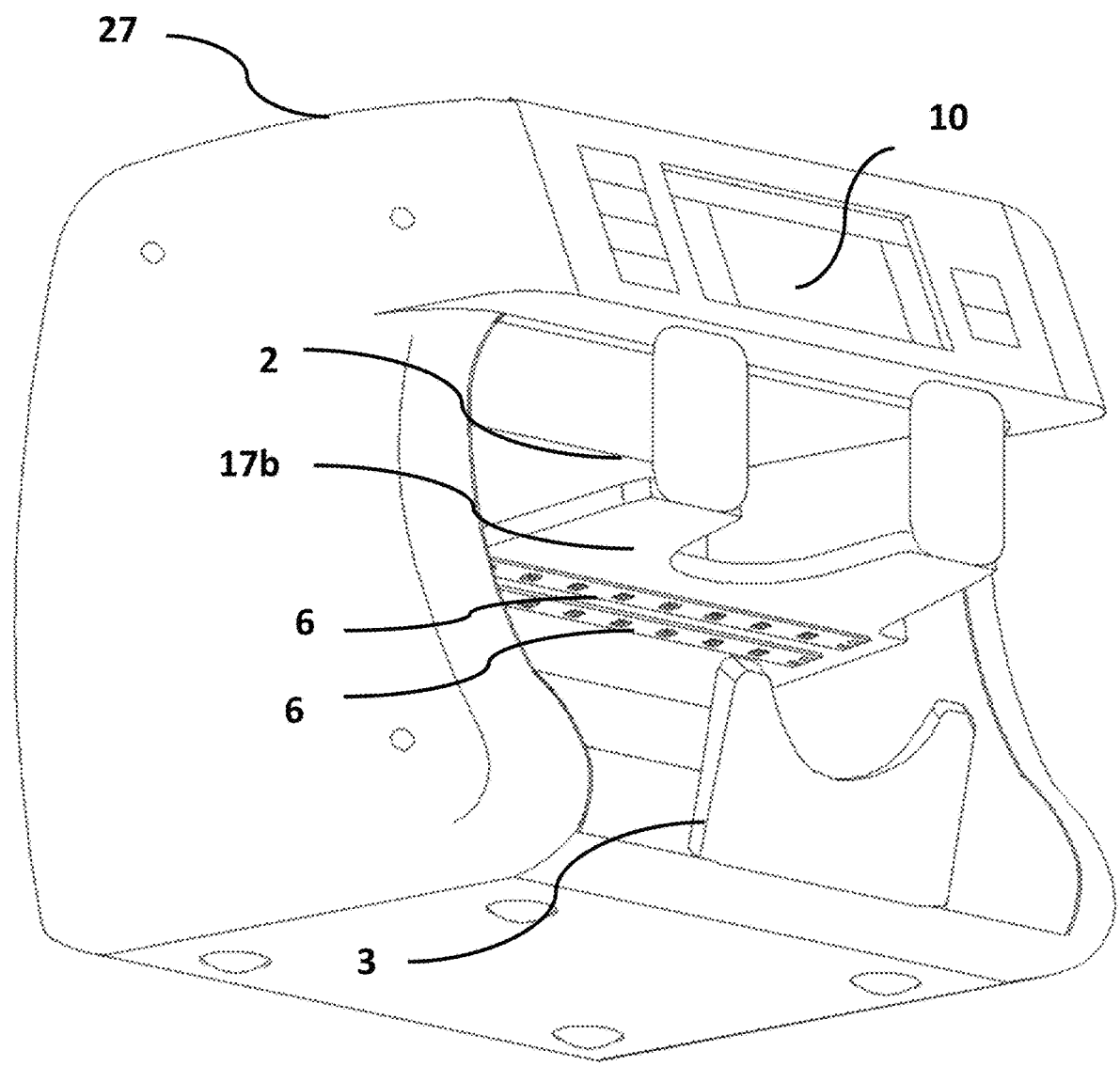

FIG. 4c is another front perspective view and FIG. 4d is another view of the currency denominating and sorting device 27 of FIG. 1 with at least one UV-C LED strip 6 which is exposed without having embedded in a container or in the container with the lens or in an enclosure. Both FIGs illustrate that UV-C LED Strip 6 without having embedded in a container or enclosure of any kind is conveniently installed underneath of the reject output receptacle 2 on the rear (opposite) side 17b and towards all the way back at the end virtually hidden from operator's eye and when reject output receptacle 2 is installed onto the currency denominating and sorting device 27 of FIG. 1, this 17b outer side/rear side of the plate installed with the at least one UV-C LED strip 6 which exposed without having embedded in a container or in container with lens or in enclosure of any kind as one of the element of embodiment of present invention faces the passing currency bills (FIG. 4c and FIG. 9) at a close distance, but virtually contactless, so that UV-C rays/radiation 6a are emitted downwardly on the passing currency bills or currency media radiating the face and on the rear side covering the entire length dimension of currency bills and contactless, thus at least reducing or eliminating various germs or the like, so that currency bills are free of microbes, germs, viruses can be handed to customers effectively and circulation to public. Due to the complex structure of currency denominating and sorting devices, if this present invention of at least one UV-C LED strip 6 will have close contact with currency bills as they pass by will damage them or jam the device resulting in a completely ineffective system for its intended purpose disinfecting them.

FIG. 4c is another perspective view and FIG. 4d is another view of the currency bills processing device 27 of FIG. 1. Both FIGs illustrate the exposed UV-C LED Strip 6 without a need for embedding in a container or enclosure of any kind can be conveniently installed underneath of the reject output receptacle 2 on the rear (opposite) side 17b and towards all the way back at the end virtually hidden from operator's eye and when reject output receptacle 2 is installed onto the currency bills processing device 27 of FIG. 1, this 17b outer side/rear side of the plate with the UV-C LED strip 6 can be exposed without the need for being embedded in a container or in the container with the lens or in an enclosure of any kind. The UV-C LED strip 6 faces the passing currency bills (FIG. 4c and FIG. 9) at a close distance, but virtually contactless, so that UV-C radiation 6a are emitted downwardly on the passing currency bills covering the entire dimension of currency bills and contactless, thus at least reducing or eliminating various germs, so that currency bills are free of microbes, germs, viruses that can be handed to customers effectively and circulation to the public.

FIG. 4ca is another partial perspective view of the preferred currency denominating and sorting device 27 of FIG. 4d with two units of UV-C LED strip 6, both strips are constructed the same way and manner, having exact same length and width dimension and both having at least 8 units of UV-C LEDs. FIG. 4ca illustrates two units of UV-C LED strip 6 exposed without having embedded in a container or enclosure of any kind and conveniently installed underneath of the reject output receptacle 2 on the rear (opposite) side 17b and towards all the way back at the end virtually hidden from operator's eye and when the reject output receptacle 2 is installed onto the currency bills processing device 27 of FIG. 4c, this 17b outer side/rear side of the plate with two UV-C LED strip 6 faces the passing currency bills (FIG. 4c and FIG. 9) at a close distance about 1 cm far apart, but virtually contactless so that UV-C radiation 6a are emitted downwardly on the passing currency bills radiating the face and on the rear side covering the entire dimension of currency bills and contactless, thus at least reducing or eliminating various germs.

Now referring to FIG. 4da, it is the same view as in FIG. 4d, but the currency bills processing device 27 of FIG. 4da is having two parallel UV-C LED strip 6. FIG. 4da illustrates the two UV-C LED strip 6 installed underneath the reject output receptacle 2 on the rear (opposite) side 17b.

Referring to FIG. 5 is a functional block diagram of an exemplary embodiment of currency bills processing device 27 of FIG. 1 which shows a general configuration of the currency bills processing device. A processor (CPU) 22 controls currency recognition unit 11 as well as authentication unit 19 and processes currency bill recognition, discrimination, and suspect detection using data memory stored into the SDRAM 21. CPU 22 connected to SDRAM 21 is programmed to count the number of currency bills, denomination of each recognized currency bill, and determine the cumulative total of the currency amount represented by the currency bills scanned through currency recognition unit 11. The CPU 22 controls the feed motor 9 and main motor 8 to convey the bills at a high speed up to 1000 bills per minute and encoder 32 controls the bill conveying mechanism 15 and bill diverter 16 to decide whether currency bills will be delivered to reject output receptacle 2 or to stacker output receptacle(s) 3 from the decision made by CPU 22. The CPU 22 is also linked to a control panel consisting of buttons or keypad or simply touch keys 10a (FIG. 1) for selection of various functionality and operation of the device and include a touch screen or LCD display unit 10 (FIG. 1. FIG. 2 and FIG. 5) display unit 10 which is adapted to provide a display of the number of bills counted, the breakdown of the bills and currency denomination, and the cumulative total of the currency value represented by counted bills. CPU 22 is also connected to an RS232 interface port 20 to connect to the printer and external display unit and (not shown here) to print the count and break-down of count as it displayed on the display unit 10. As to currency media, after successfully reading and decoding the currency recognition unit 11 and processed by CPU 22 and EPROM 20, results may display on the display unit 10 or to a printer connected to it or transfer results to a PC software connected via RS232 interface port 20 which are known in the art. After encoder 32 diverts the currency bills, the currency bills can then pass under at least one UV-C LED strip for instant disinfection prior to delivering currency bills to stacker output receptacle(s). The CPU 22 is also connected to a power supply unit 5 to supply electric power to motors 8 and 9 and currency recognition unit 11. The power supply unit 5 has a fan 14.

Figure 6:
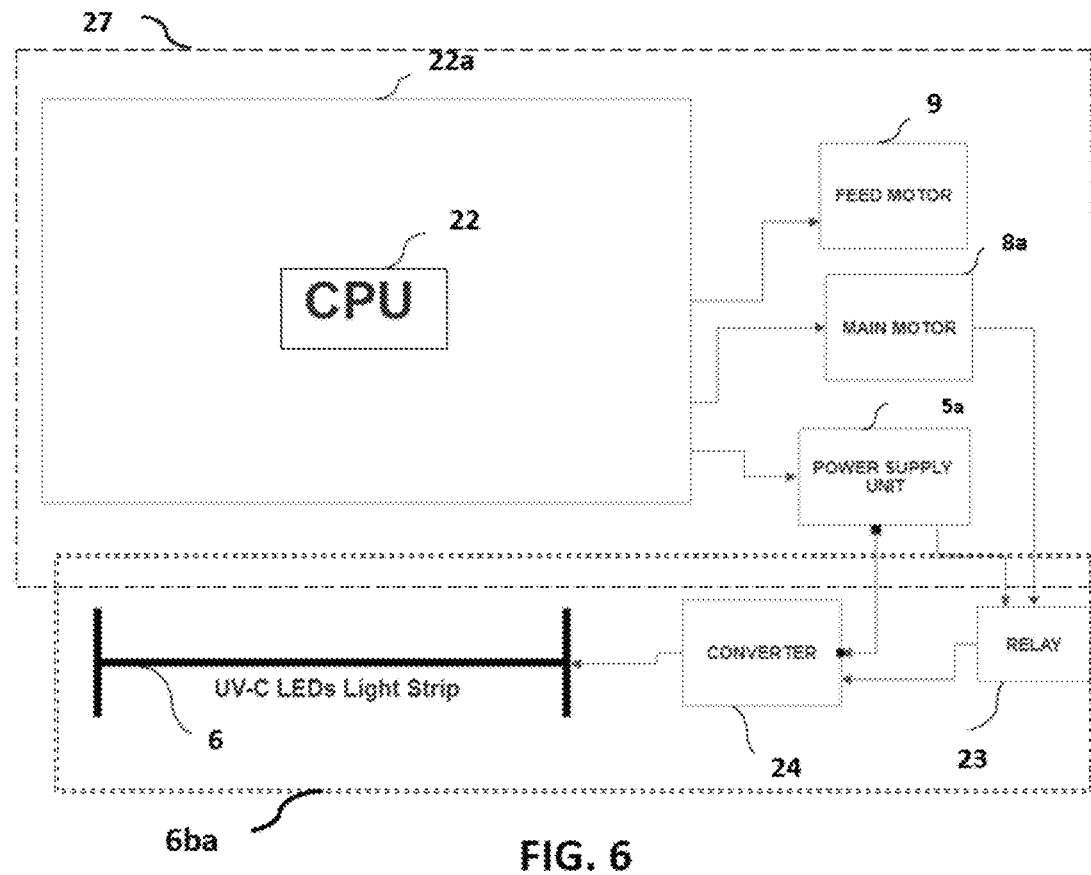
FIG. 6 is another functional block diagram of the currency bill processing device, according to an exemplary embodiment of the present invention.

Referring now to block diagrams in FIG. 6 and FIG. 7b illustrates the disinfecting unit 6ba and 6b respectively that can be mounted in the currency bills processing device 27 shown in FIG. 1. In one case, the UV-C LED strip 6 utilizes minimal electric current obtained through connecting to a DC VOLTAGE converter 24 which is connected to main motor power supply circuit 8a of the currency bills processing device 27 (FIG. 1) and a relay 23 is engaged as a part of the system of the current invention. Relay 23 is connected to Power supply circuit 5a and the main motor power supply circuit 8a located on the mainboard 22a of the currency denominating and sorting device 27 of FIG. 1. Relay 23 is connected to main motor power supply circuit 8a to determine when disinfecting unit 6b can be activated (when it is energized) and starts to emit UV radiation with a frequency of about 269 nm at its peak on the passing currency bills.

The UV-C LED strip 6 only activates when main motor 8 starts conveying the currency bills through conveying path 15a, 15b, 15c (FIG. 3). Until then, the relay remains de-energized and the disinfecting unit 6b remains off.

Figure 7A:
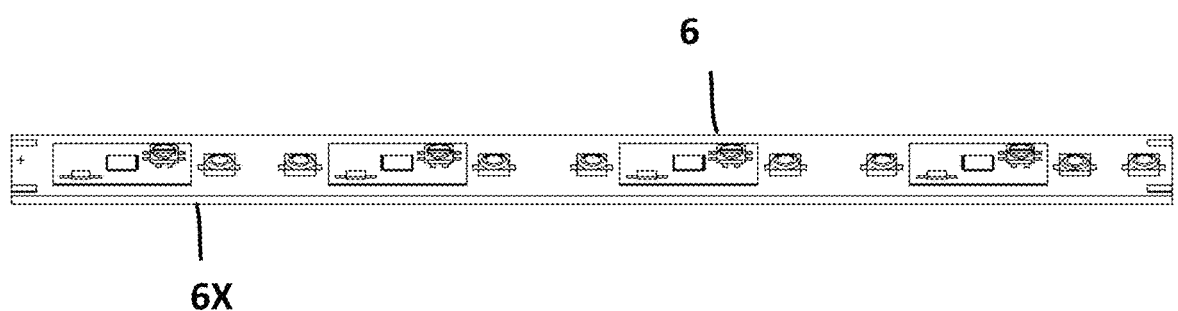
FIG. 7a shows the UV-C LED strip, according to an exemplary embodiment of the present invention.
Figure 7B:
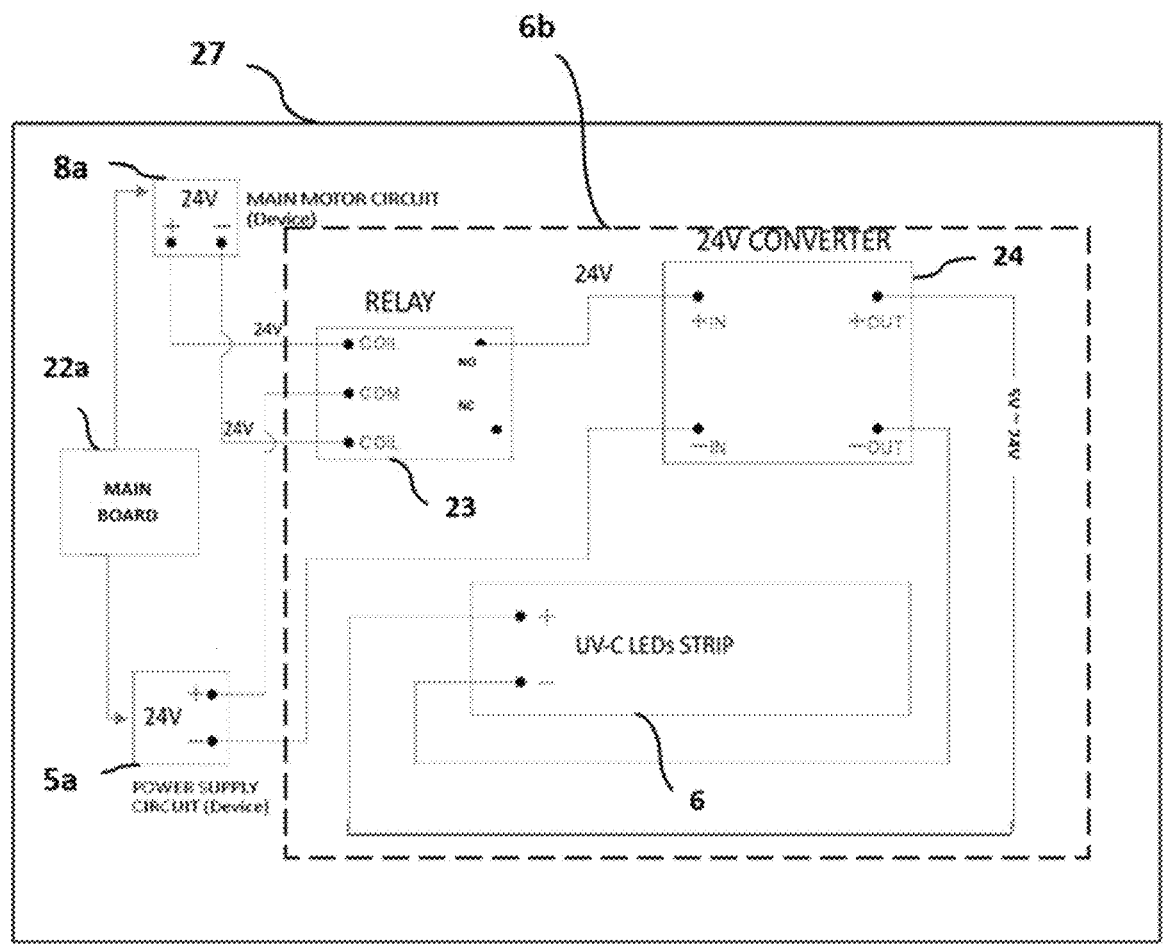
FIG. 7b is an electrical circuit diagram of the currency bill processing device, according to an exemplary embodiment of the present invention.
Figure 7B:
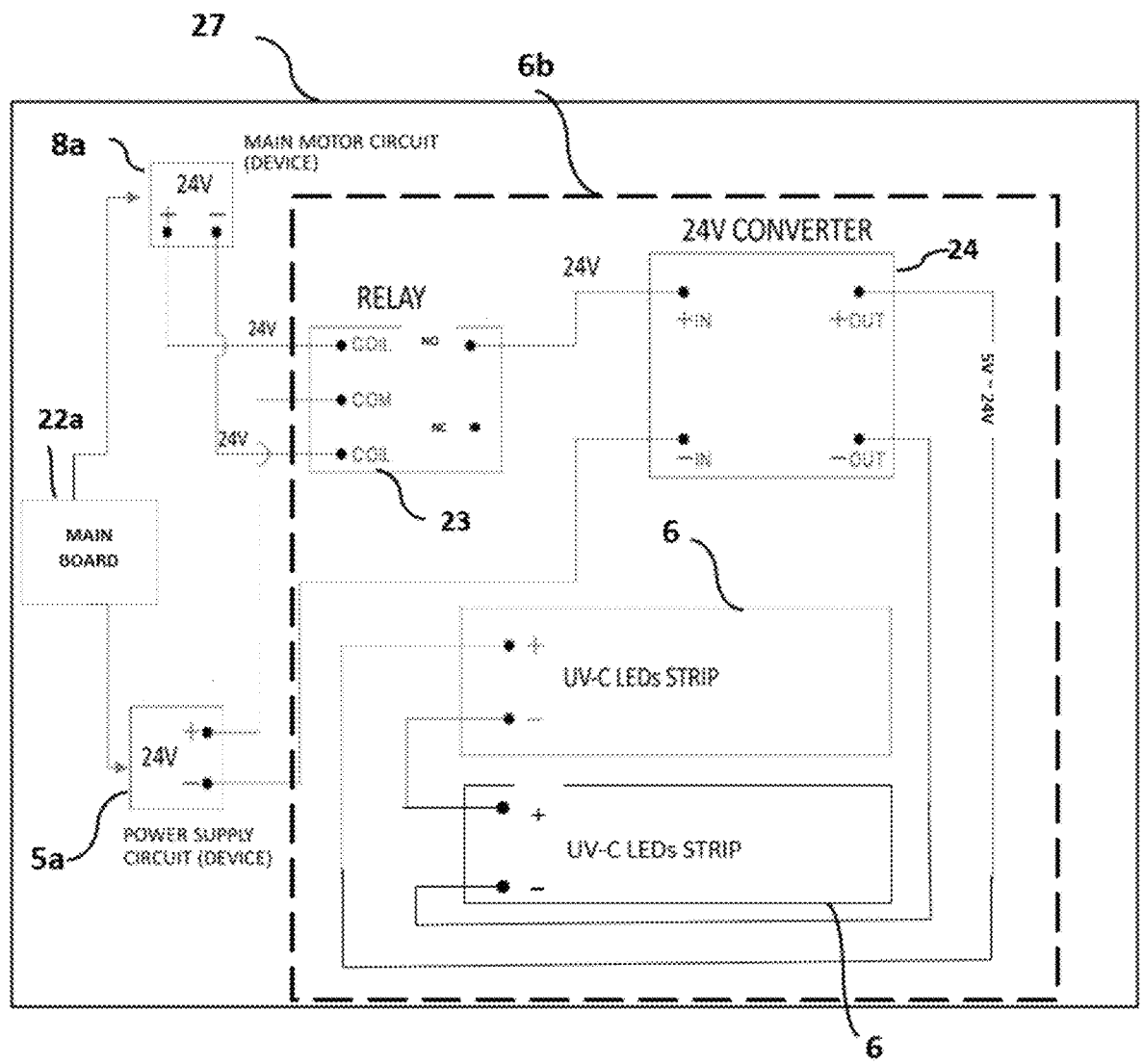

Referring to FIG. 7a, which shows the UV-C LED strip 6 mounted on a rigid aluminum or copper base 6X. the base 6X can be at least 1 mm in thickness. The UV-C LED strip 6 can be at least 7 inches in length and at least 0.5 inches in width. Preferably, each UV-C LED strip 6 can have at least eight UV-C LEDs arranged linearly along the length of the UV-C LED strip. It is understood that the number of the UV-C LEDs in a single UV-C LED strip and arrangement of the UV-C LEDs can vary without departing from the scope of the present invention. For example, 12 units of UV-C LEDs can be used. However, it may be preferable to have at least eight UV-C LEDs for desired disinfection of the currency bills. Moreover, the dimensions of the base 6x can be more than 7 inches depending on the space available on the reject receptacle as described for FIG. 4b, however, cannot be less than the length of the currency bill being disinfected. For the desired disinfection, it is preferable to cover the entire length of the currency bill.

Referring again to the block diagram in FIG. 7b illustrating the disinfecting unit 6b. The disinfecting unit 6b includes at least one UV-C LED strip 6 mounted on an aluminum or copper base and consisting of at least eight UV-C LEDs, a 24V DC step-down voltage converter 24 and a relay 23. The UV-C LEDs can generate radiation in a spectrum that can kill or inactivate the microorganisms. The power supply circuit 5a of the currency bills processing device 27 can supply 24V current, one skilled in the art would understand that currency denominating devices may supply different current from their power supply circuit depending on the overall electrical design of the devices, for example, some currency denominating devices may output 12V from their power supply circuit. The disinfection unit may also be configured to receive necessary voltage, such as 5V, or 12V, or 24V needed to operate and obtained from the power supply circuit 5a of the currency bills processing device. FIG. 7b illustrates that the UV-C LED strip configured with anywhere from 5V~24V depending on how many UV-C LEDs are installed on the strip and receiving necessary current needed to operate by coupling the UV-C LED strip 6 to a voltage converter 24 and one skilled in the art would understand that a voltage converter may not be needed in case the UV-C LED strip 6 can use 24V current to operate. In an alternate embodiment, the UV-C LED strip can be directly connected to the power circuit 5a. Relay 23 is used to activate or deactivate the UV-C LED strip 6 by switching power on and off from the main motor power circuit 8a and power supply unit 5. The relay 23 is connected to power supply circuit 5a and main motor power supply circuit 8a located on the mainboard 22a and energizes when main motor 8 starts to run the conveying mechanism and supply continuous current to the converter which can then be converted to desired voltage necessary to operate the UV-C LED strip 6. Such Relay and a DC voltage converter and how they function are well-known in the art, and not explained in detail. The UV-C LED strip 6 becomes inactive when the relay is de-energized. Therefore, the disinfecting unit 6b does not need a separate battery source or separate power source. Since UV-C LED strip 6 activates and deactivates based on the signal receiving from main motor 8 by the relay 23, therefore, the disinfecting unit 6b does not require operator's manual intervention, such as pressing any keys or buttons on the control panel 10a (FIG. 1) to activate or deactivate the UV-C LED strip 6. The operator can simply operate the currency bills processing device similar to known currency denominating and sorting devices and receive the disinfected currency bills.

Now referring to the block diagram in FIG. 7ba showing the disinfecting unit having two UV-C LED strip 6. The two UV-C LED strip 6 can be similar in dimensions and mounted to a common or different aluminum or copper base. Two UV-C LED strips can be connected to each other and to the common power supply through a DC step-down voltage converter 24 or directly connected to the device 27 power supply circuit 5a in case of 24V configured UV-C LED strip 6. The disinfecting unit 6b includes a relay 23 as described in detail in FIG. 7b.

Figure 7C:
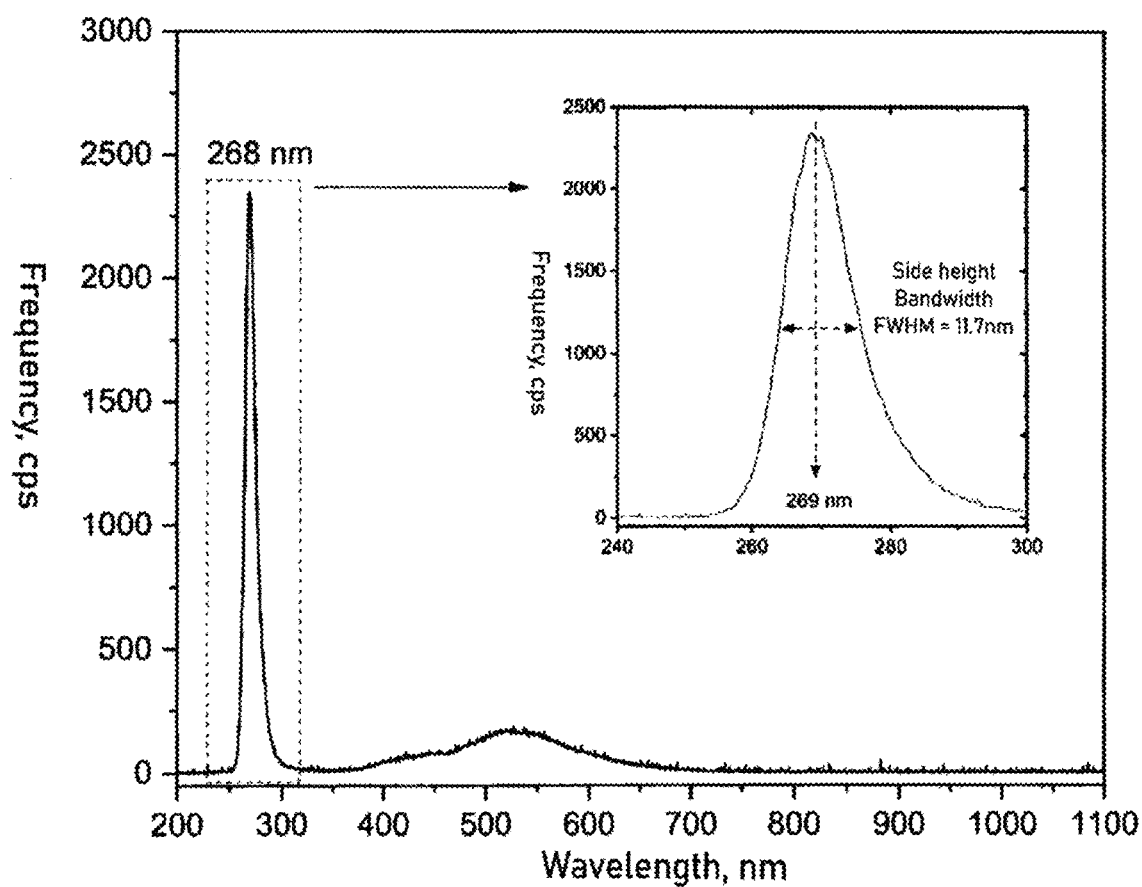
FIG. 7c is a spectrogram representation of the frequencies and wavelength of preferred germicidal UV-C LEDs at their peak of 269 nm wavelength.

Referring now to FIG. 7c is a spectrogram representation of the frequencies and wavelength of UV-C LEDs showing the peak of 269 nm. It is well established that UV radiation in the wavelength range of about 269 nm is effective in germicidal applications and at least partially reduces or eliminates various germs that may have settled and inhabited on the surface of the currency bills instantly at a speed of up to 1000 bills per minute.

Figure 7D:
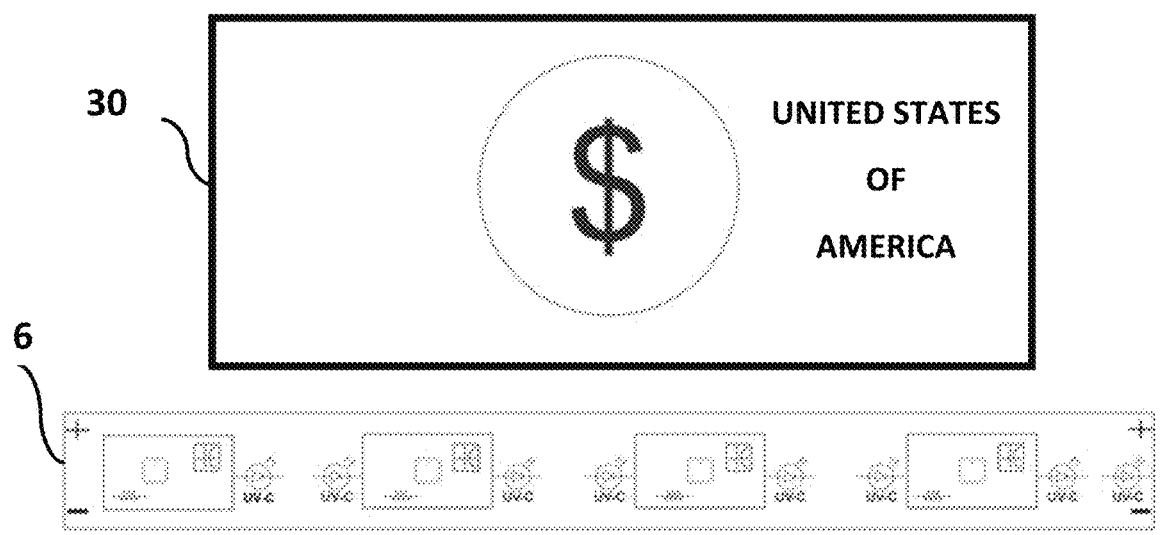
FIG. 7d shows a comparison of a length of a standard U.S. Dollar currency bill with the UV-C LED strip, according to an exemplary embodiment of the present invention.
Figure 7E:
FIG. 7e shows a comparison of a casino ticket with the UV-C LED strip, according to an exemplary embodiment of the present invention.

FIGS. 7d and 7e illustrate the comparison between the UV-C LED strip 6 with a US dollar 30 as the currency bills in FIG. 7d and a casino ticket 31 as the currency bill in FIG. 7e.

Figure 8:
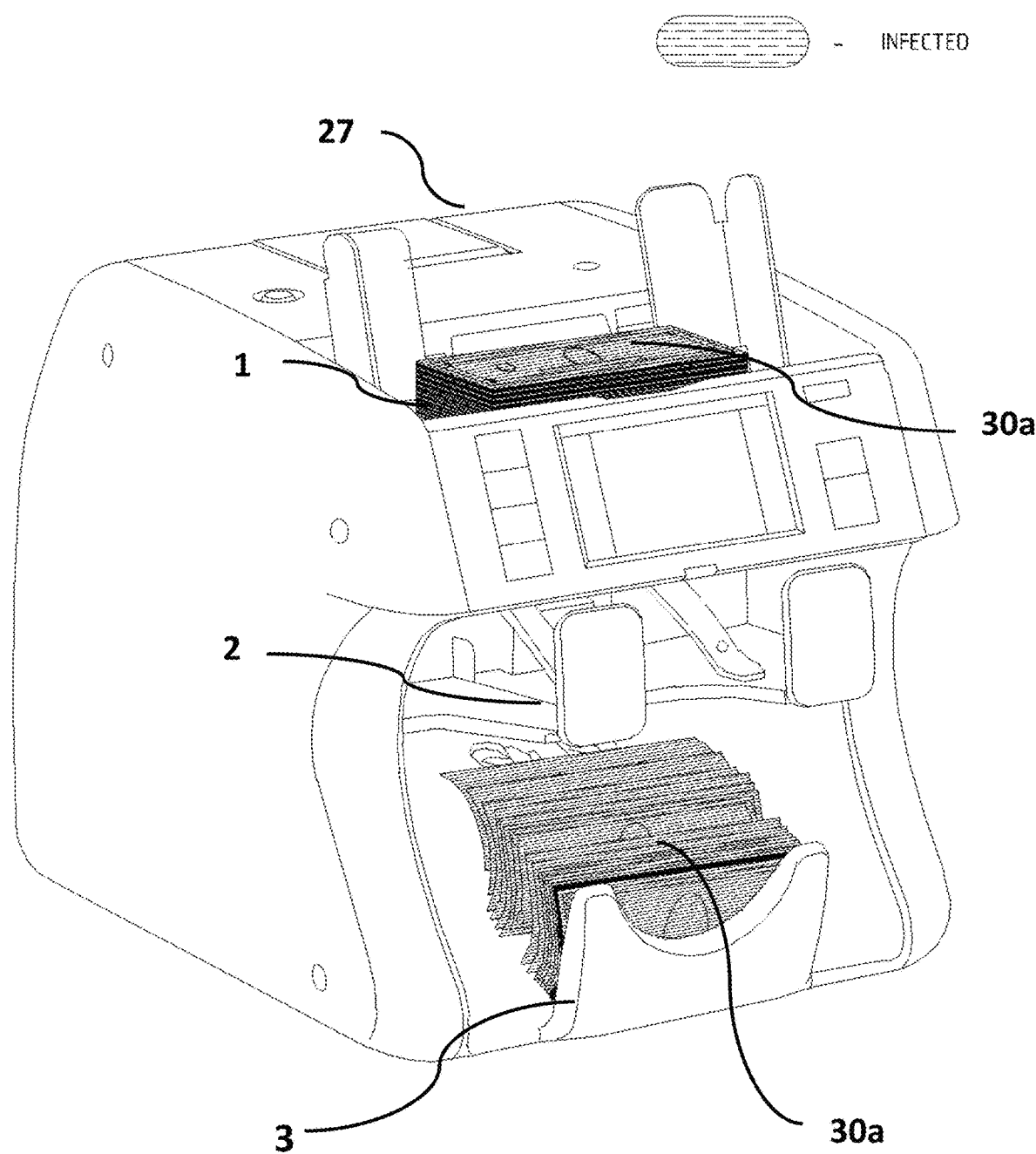
FIG. 8 shows a currency bill processing device as in FIG. 1 further illustrating the passing of the currency bills through the device and without having a UV-C LED strip.

Turning to FIG. 8, it is a perspective view of a denominating and sorting device 800 not having the disinfecting unit and further showing the infected and contaminated currency bills 810 placed on the bill input station 820 and processing without being sterilized and disinfected as in usual practice in cash handling industry. Currency bills in circulation are never sterilized or disinfected before handing them over to a customer or to bank tellers or cash register tellers or cash transactions at various retail outlets, casinos, or gaming where cash is involved. Those who are accepting currencies in the transaction or processing them are subject to get infected by various germs among others which are settled in and accumulated over a period and inhabit the surface of a paper currency bill or paper media for many days.

Figure 9:
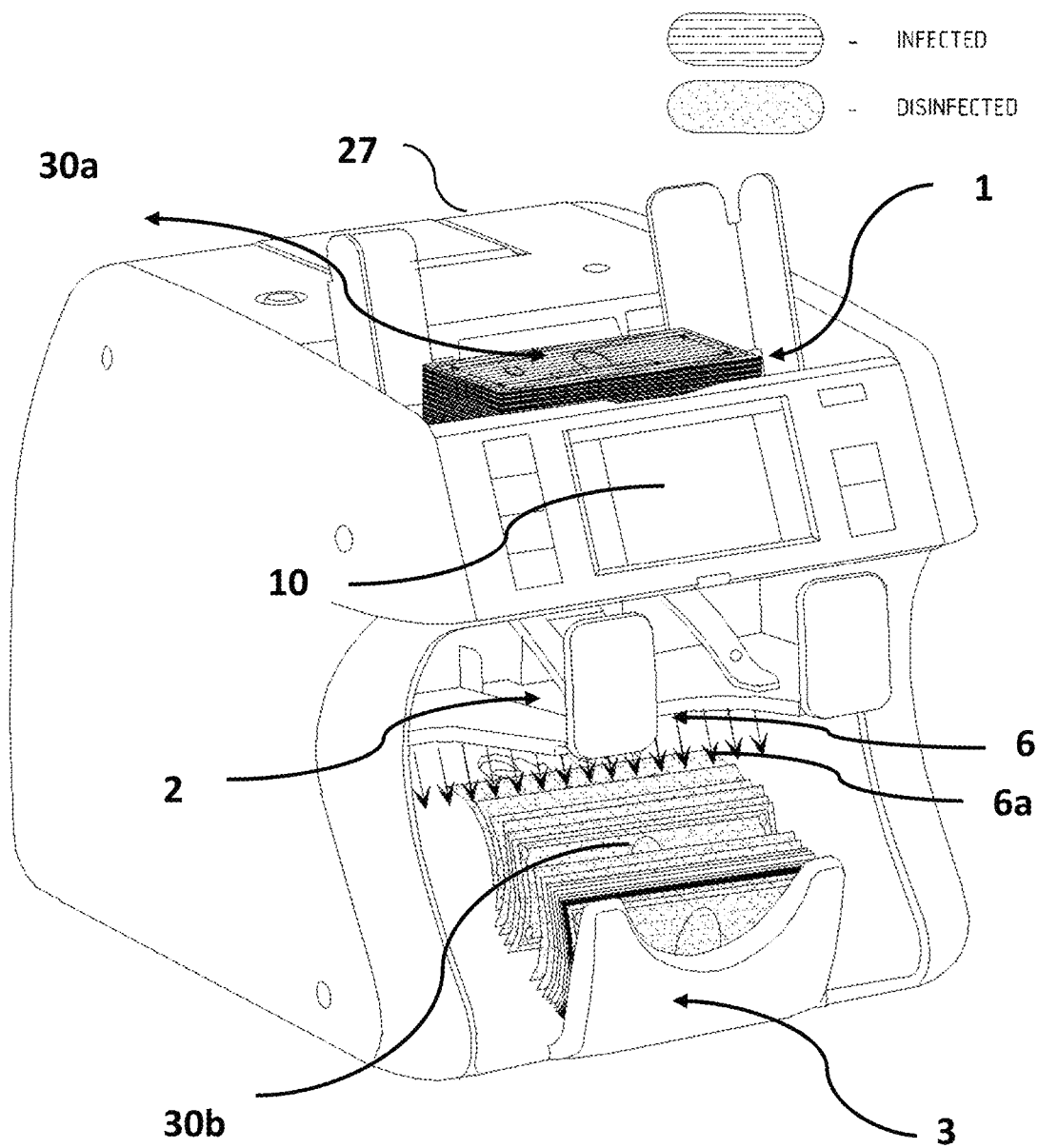
FIG. 9 shows the currency bill processing device as in FIG. 1 further illustrating the passing of the currency bills and are being disinfected by the UV-C irradiation (shown by downward arrows), according to an exemplary embodiment of the present invention.

Unlike the denominating and sorting device 800, FIG. 9, which shows the UV-C LED strip 6 installed in the currency bills processing device 27. FIG. 9 further illustrates the infected currency bills 30a on the bill input station 1 and after they are disinfected by the UV-C LED strip 6 and then conveyed and diverted to stacker output receptacle 3. FIG. 9 shows currency bills 30b passing under the UV-C LED strip 6 and irradiated by UV-C radiation 6a at a frequency of about 269 nm at its peak, are disinfected and sitting on the stacker output receptacle 3 free of germs, so that they can be handed to customers by bank tellers or clerks of the cash register at various retail outlets, restaurant-bar-nightclubs, casinos and gaming among other places use cash as the primary source of exchange.

Figure 9A:
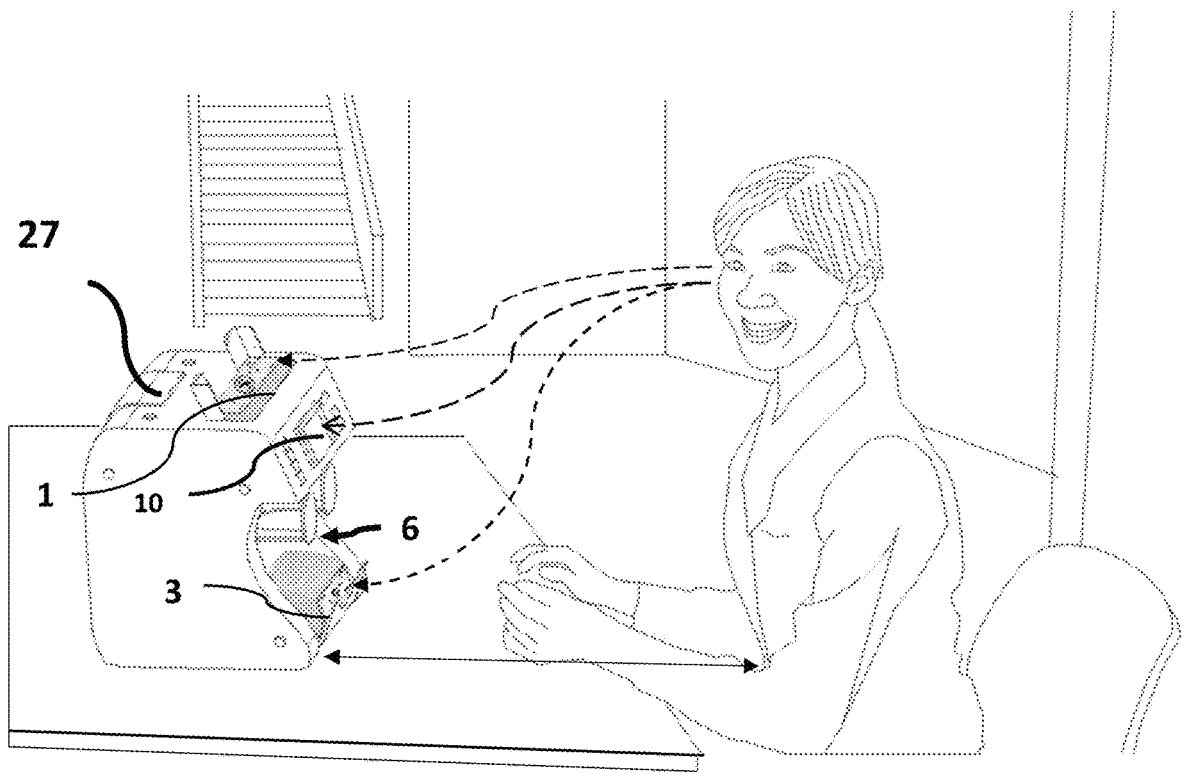
FIGS. 9a and 9b show a working environment of the currency bill processing device as in FIG. 1 placed on a teller counter-desk while teller is sitting about 1-1.5 feet away from the currency bill processing device and the operator is not exposed to the UV-C radiation from the currency bill processing device, according to an exemplary embodiment of the present invention.
Figure 9B:
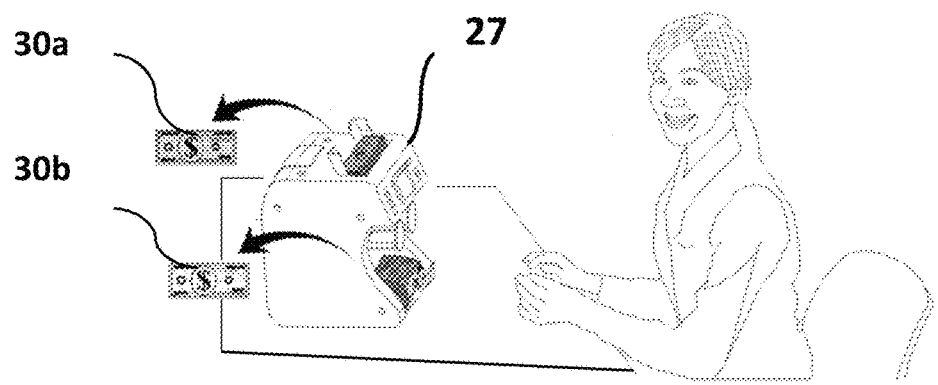

Referring to FIGS. 9a and 9b, illustrate the currency bills processing device placed on a teller counter-desk where bank tellers usually operate the currency bills processing device from about 1-1.5 feet far distance from sitting position. FIGS. 9a and 9b further illustrate that the UV-C LED strip 6 installed underneath (outer side) the reject receptacle plate 17b is hidden from the operator's eyes. The operator usually focuses on the display unit 10 of the device to see counting results during the processing of currency bills or look at the stacker output receptacle 3 (FIG. 1) to see if currency bills 30 (FIG. 9) and 31 (FIG. 10) are stacking properly or jammed there. The operator generally never looks underneath or outer side of the reject output receptacle plate 17*b* (FIGS. 4*c* and 4*d*) where the UV-C LED strip 6 is installed. It is also envisioned that operators can be supplied with, or operator can purchase their own UV-C rated safety glass to wear when operating the currency denominating devices installed with UV-C LED strip 6, element of embodiments of the present invention if there is any safety concern. Even the operator may bend down and look underneath or outside side of the reject receptacle plate 17*b* (FIGS. 4*c* and 4*d*), they will still be at least 1½ feet far distance from the UV-C LED strip 6 (FIGS. 4*c* and 4*d*). FIG. 9*b* further illustrates that infected currency bills 30*a* placed on the top of the bill input station 1 (FIG. 9*a*) and then infected currency bills 30*a* are disinfected by irradiating them with UV-C radiation downwardly using the UV-C LED strip 6 (FIGS. 4*c* and 4*d*) prior delivering them to the stacker output receptacle 3.

Figure 10:
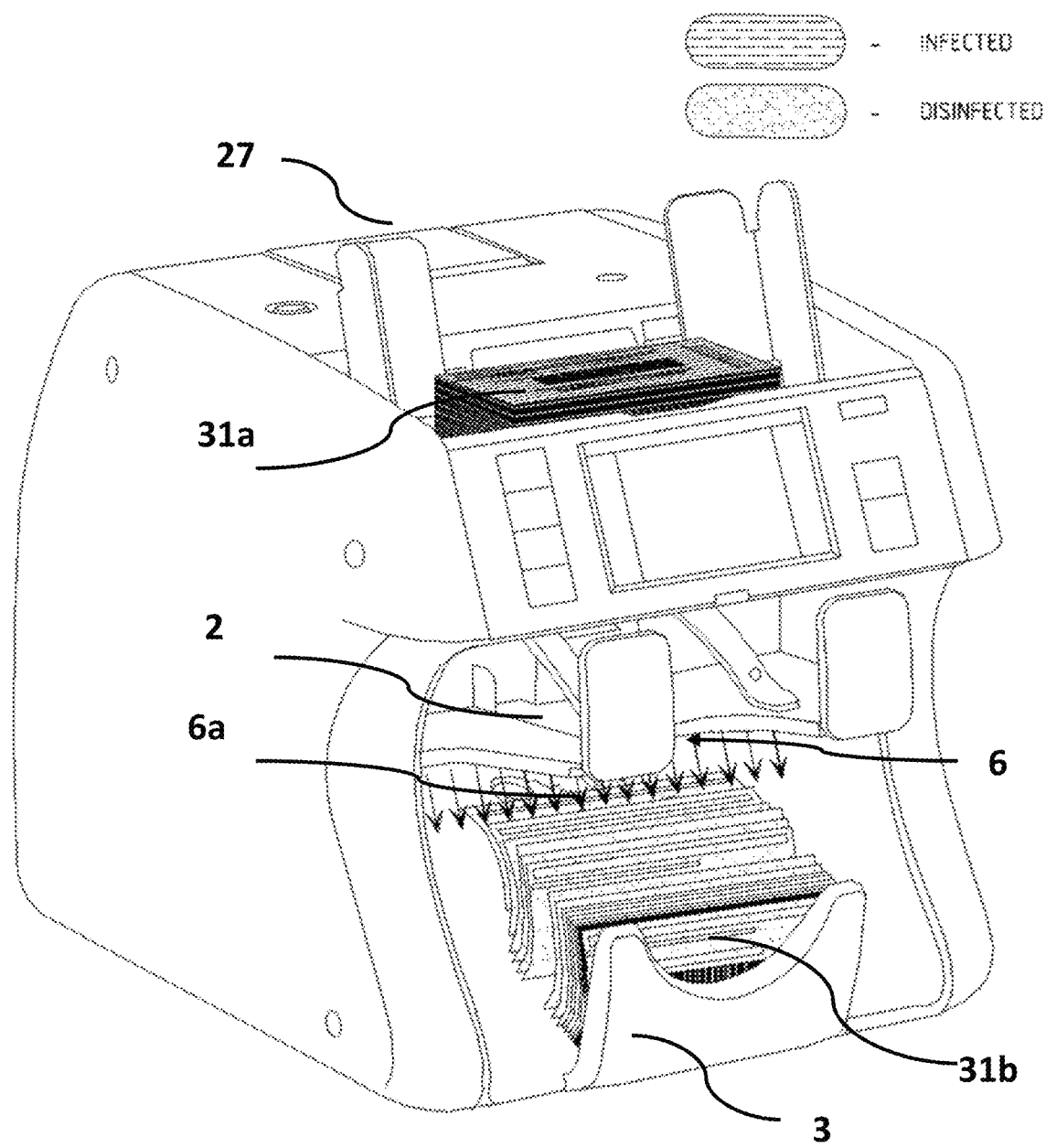
FIG. 10 is a perspective view of the currency bill processing device as in FIG. 1 showing the casino tickets with barcode feature being disinfected by UV-C irradiation, according to an exemplary embodiment of the present invention.

Referring to FIG. 10, shows the currency bills processing device 27 demonstrating infected and disinfected currency bills 31*a*, such as casino barcoded tickets. Possibly casino tickets received from customers (came out from slot machines etc.) are infected with microbes. These infected currency bills can be processed through the disinfecting unit 6*b* for disinfection and then deliver to the stacker output receptacle 3 for casino clerks to pick up and send to the back-office for further validation and processing and storage. These tickets are dispensed by casino slot machines and then redeemed for cash at the cash counter in casinos and other gaming avenues. These tickets must be processed by casino staff for validation and then storage. Therefore, chances of contamination risks exist greatly and place the casino staff at risk of being infected if they are not disinfected before handing them.

Figure 11:
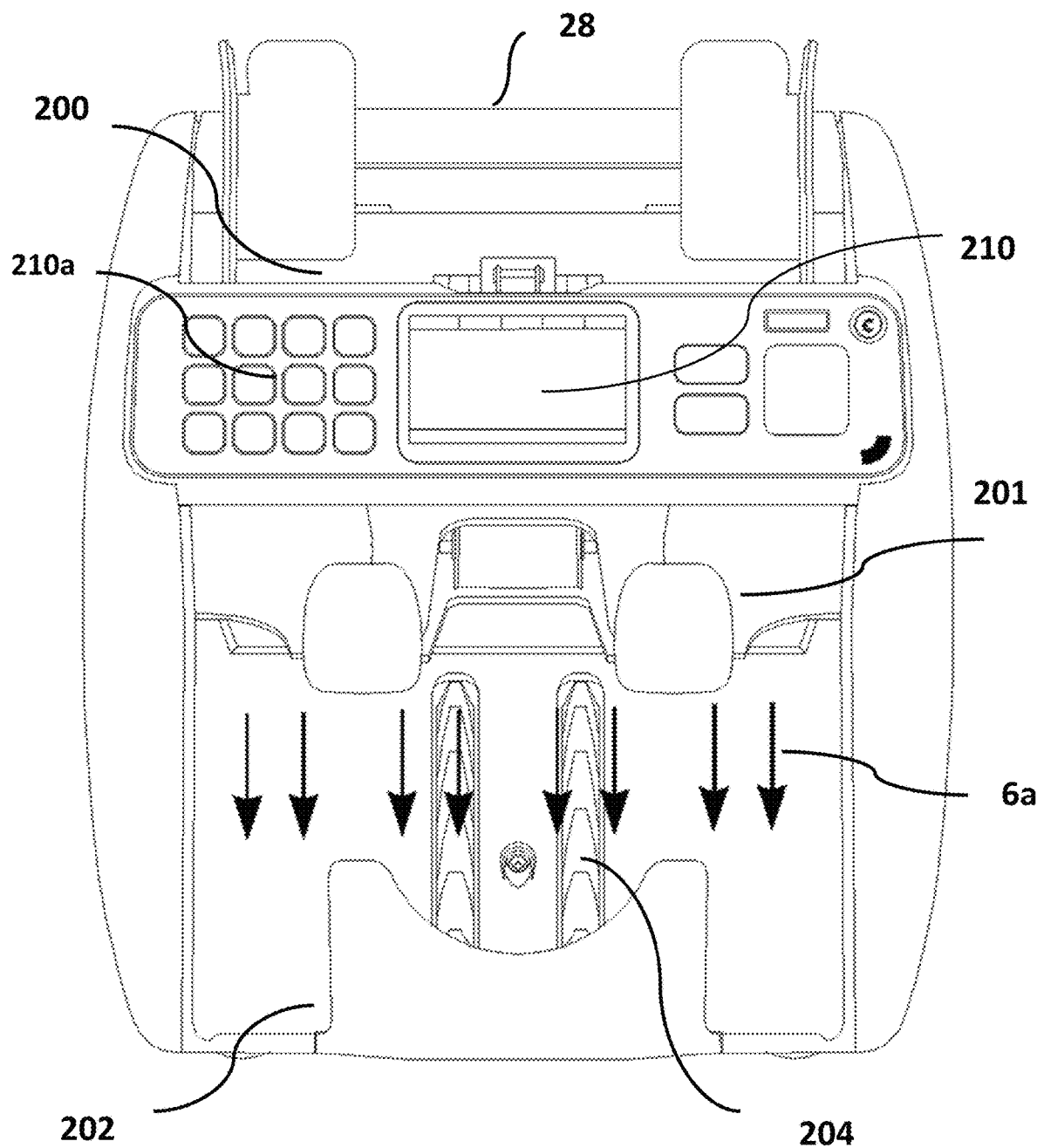
FIG. 11 is a perspective view of an alternative embodiment of the currency bill processing device having a single stacker output receptacle, a reject output receptacle, and the disinfection unit, according to an exemplary embodiment of the present invention.
Figure 12:
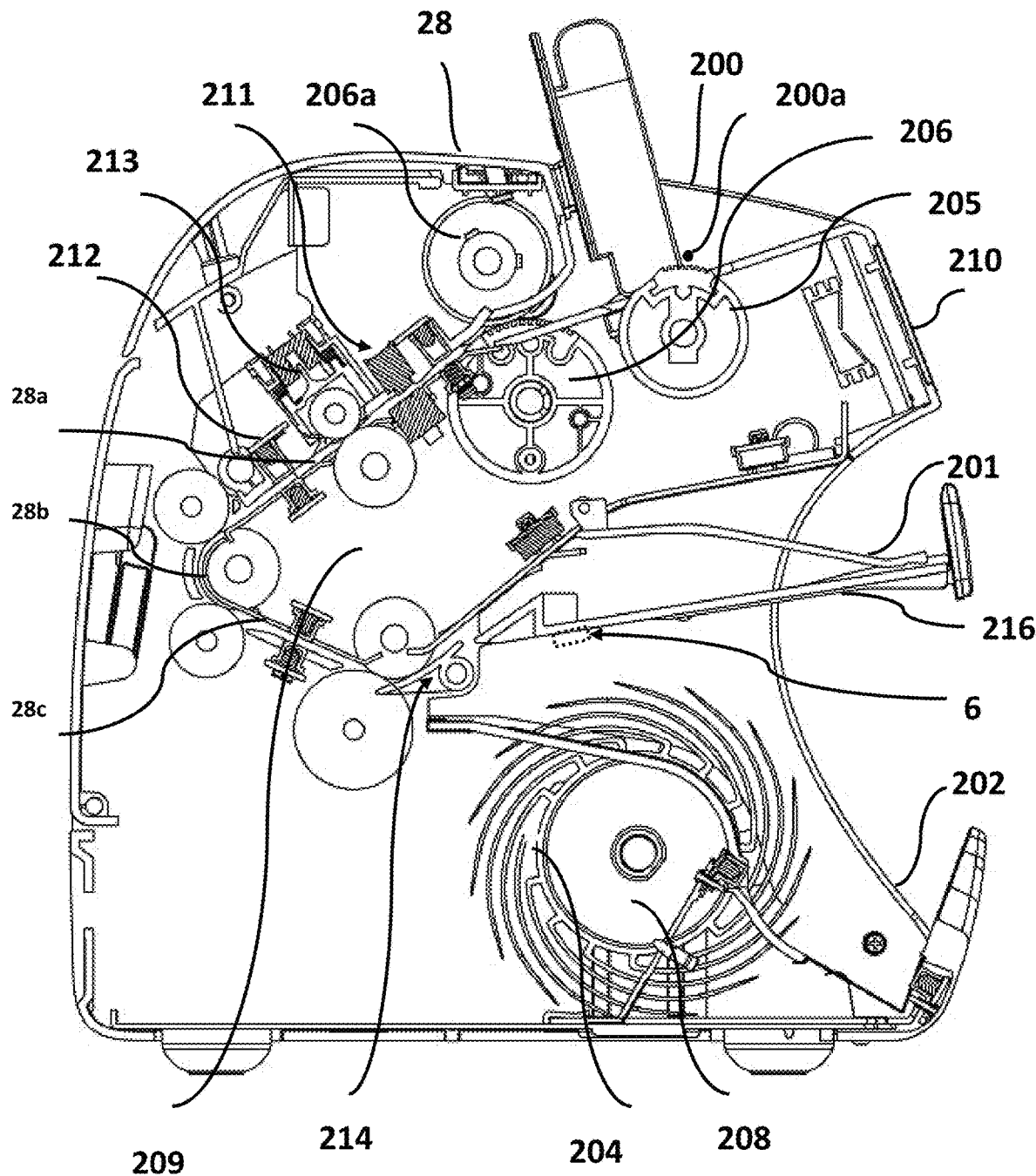
FIG. 12 is a cross-sectional view of the currency bill processing device shown in FIG. 11, according to an exemplary embodiment of the present invention.

Referring now to FIG. 11, it is a perspective view of an alternative embodiment of the currency bills processing device 28, and FIG. 12 is the internal view of the currency bills processing device 28. The currency bills processing device 28 is structured, design, and works under the same principle and functionality as the currency bills processing device 27, but slightly smaller in dimension having 11" width, 10.7" length, and 10.3" height. The currency bills processing device 28 also includes a bill input station or receptacle or bill input station 200 where a stack of currency bills that need to be discriminated, recognized, and counted are placed. Currency bills in the bill input station 200 are acted upon by a bill sensor 200*a* (FIG. 12) to sense that there is an object placed on the bill input station 200 and once sensed, currency bills then start to feed and convey using of combination of feed rollers 205, 206 and 206*a* and feed motor (not shown in the drawings) one currency bill at a time with the narrow dimension of the currency bills being parallel to the bill input station 200 and currency recognition unit 211 (FIG. 12). Currency bills then pass the currency recognition unit 211 (FIG. 12) and several authentication units, such as ultraviolet light 212 and magneto-resistive (MR) sensor 213 where the currency bill is recognized, denomination of the bill is identified and discriminated, suspect detection checking is performed, and in case of currency media such as casino tickets, they are decoded for their printed barcode feature or reading of MICR (magnetic ink character recognition) in case of banknote check. It is well-known in the art that substitutes currency media are not subject to this authentication checking due to characteristics of currency media. Once judgment is made by the currency recognition unit 211 (FIG. 12) as to the denomination and value of the currency bills are properly recognized, read, and decoded, then currency bills then conveyed forward using of currency bills conveying mechanism at a speed up to 1000 bills per minute through bill conveying path 28*a*, 28*b*, 28*c* (FIG. 12).

The currency bill conveying mechanism usually consists of many small rollers and shafts and the main motor (not showing on the diagram) to drive currency bills through conveying paths 28*a*, 28*b*, 28*c* (FIG. 12) at a high speed. Although FIG. 12 shows many rollers on the conveying path as a part of the currency bills conveying mechanism, the structure of such high-speed currency bills conveying mechanism is well-known in the art and so is not describe herein in detail. The next step would be for currency bills to pass under the UV-C LED strip 6 (FIG. 12) which is located underneath the reject output receptacle 201 in opposite direction 216, and structure and method have been described in great detail in FIGS. 4*a* and 4*b*, thus being disinfected via UV-C radiation 6*a* (FIG. 11, FIG. 13) prior currency bills are delivered to single stacker output receptacle 202 based on the judgment made by the currency recognition unit 211 (FIG. 12). The main stacker output receptacle 202 is equipped with a pair of stacker wheel 204 and stacker motor 208 for stacking the currency bills in alignment. If a passing currency bill is not recognized, then it is diverted to a reject output receptacle 201 (FIG. 11. FIG. 12). As will describe below, alternative device 29 (FIG. 15) includes more than one stacker output receptacle and would collaborate with the same principle of the present invention.

One skilled in the art of currency processing devices would understand that currency denominating and sorting devices include a mainboard 22*a* (FIG. 5, FIG. 6) and a CPU (not showing here) but illustrated in FIG. 5 and FIG. 6 for the same currency bills processing device 27. As described above, CPU is adopted to program to count the number of currency bills, denomination of each recognized currency bill and determine the cumulative total of the currency amount represented by the currency bills scanned through currency recognition unit 211 (FIG. 12). The CPU is also linked to a control panel consisting of buttons or keypad 210*a* (FIG. 11) for selection of various functionality and operation of the currency bills processing device and include an LCD display unit 210 (FIG. 11, FIG. 12) which is adapted to provide a display of the number of currency bills counted, the breakdown of the currency bills and currency denomination, and the cumulative total of the currency value represented by counted currency bills. The display unit 210 can also be adapted to supply a print-out of the displayed information in the desired format. CPU also connected to RS232 interface ports (not shown) to connect to printer and external display unit (not showing) to show the count and break-down of count as it displayed and conventional. As to currency bills, after successfully read and decoded by the currency recognition unit 211 and processed by CPU and EPROM as illustrated in FIG. 5 for the same currency denominating and sorting device 27, results may display on the display unit 210 or to a printer connected to it or transfer results to a PC software connected via RS232 interface port located at the rear side of the device 28.

Figure 13:
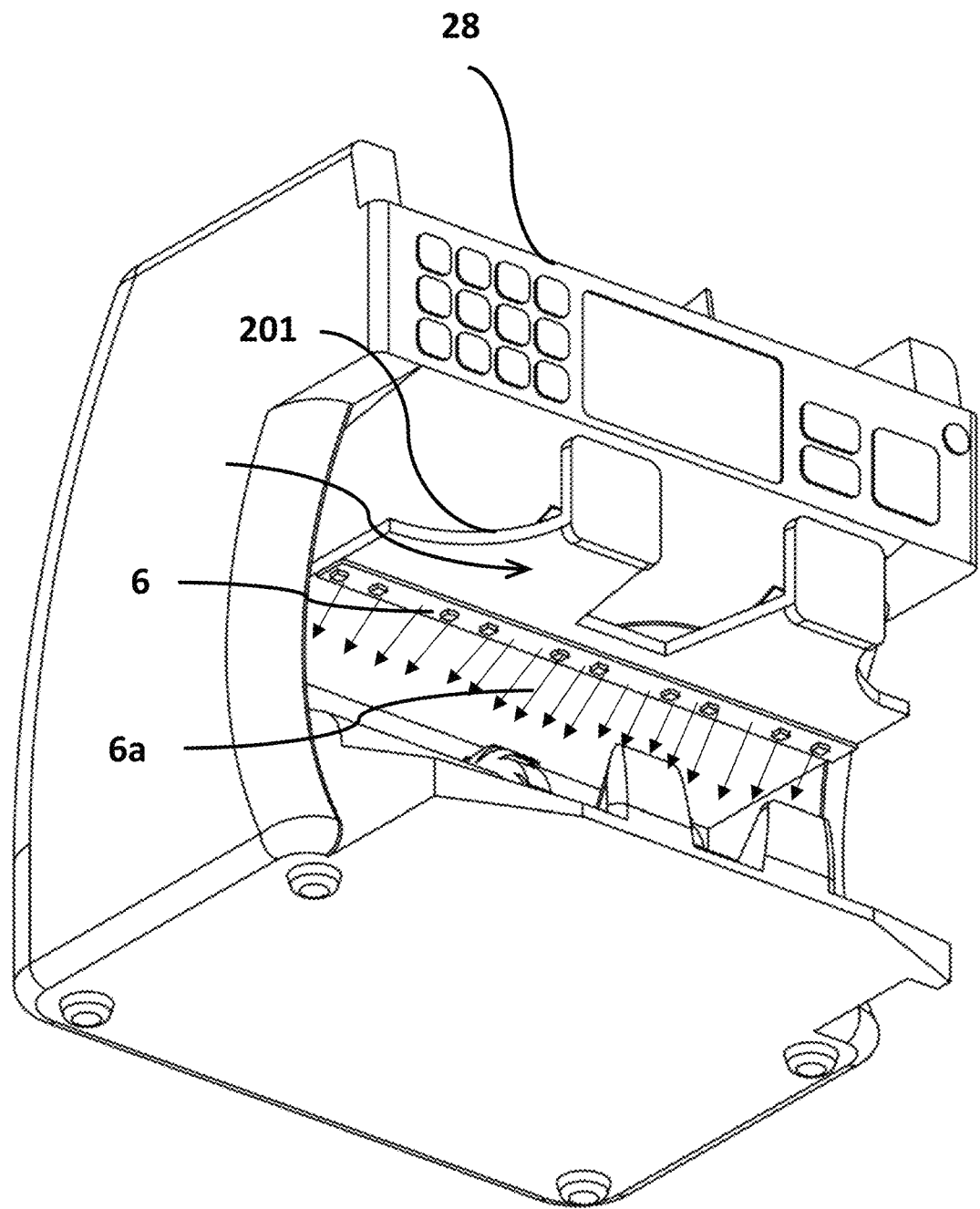
FIG. 13 is another perspective view of the currency bill processing device shown in FIG. 11, according to an exemplary embodiment of the present invention.

Referring to FIG. 13, which shows the currency bills processing device 28 of FIG. 10, illustrating that UV-C LED strip 6 is about 7 inches length and 0.5 inches in width is conveniently installed underneath (outer side) 216 of the reject output receptacle 201 and receptacle on the outer/opposite side having dimension itself of at least 7.5 inches in length and 6 inches in width, therefore, outer/opposite side 216 of reject output receptacle 201 is large enough to allow 7 inches UV-C strip bar to be installed conveniently and on the smooth area towards all the way at the end of the plate virtually hidden from operator's eye and when reject output receptacle 201 is installed onto the currency bills processing device 28, this 216 side along with the UV-C LED strip 6 faces the passing currency bills (FIGS. 13 and 14) and also previously illustrated in FIG. 9 of currency bills processing device 27, so that UV-C radiation 6a are emitted downwardly on the passing currency bills radiating the face and on the rear side covering the entire dimension of currency bills, thus at least reducing or eliminating various germs.

Figure 14:
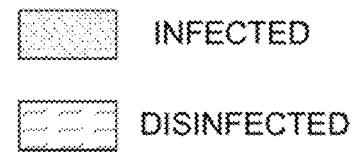
FIG. 14 shows the currency bill processing device of FIG. 11 further illustrating the irradiation of the currency bills, according to an exemplary embodiment of the present invention.
Figure 14:
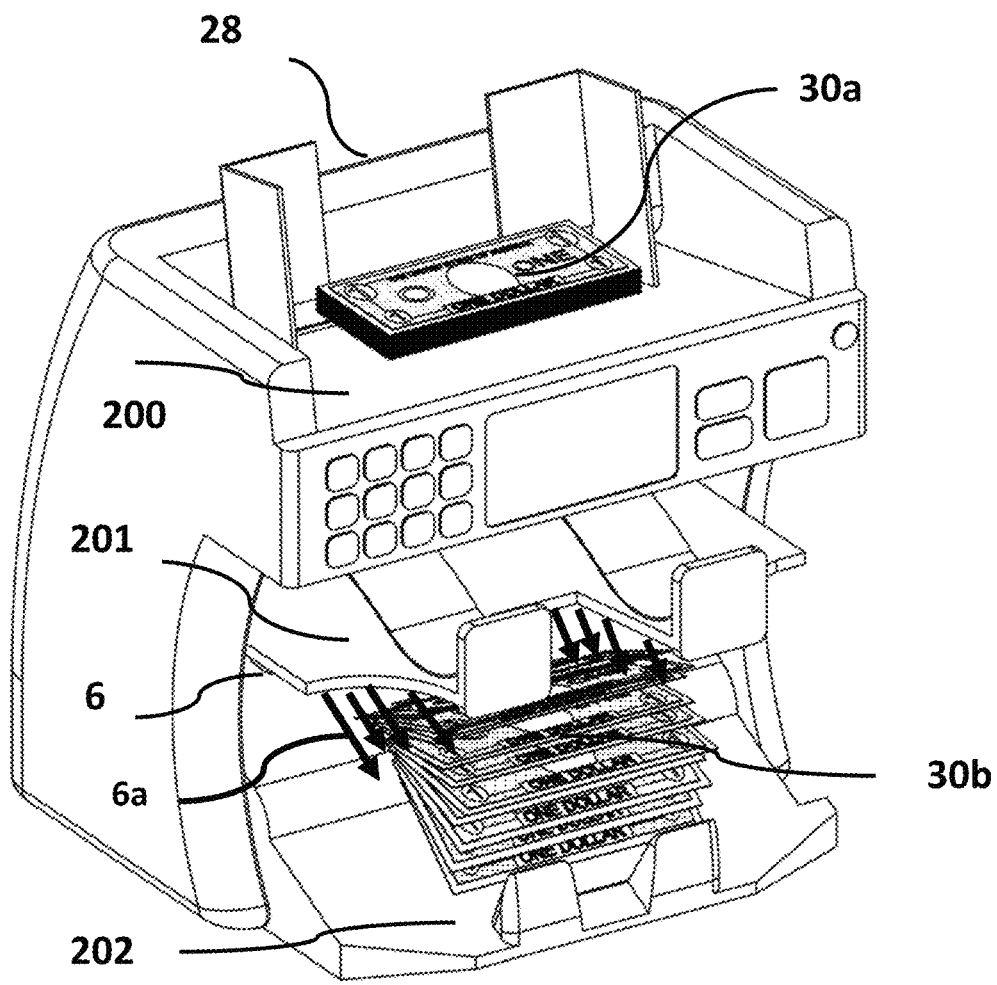

Referring now to FIG. 14, the currency bills processing device 28, an illustration is made showing infected currency bills 30a on the bill input station 200 and after they are disinfected by the UV-C LED strip 6, irradiated by UV-C radiation 6a at a frequency of about 269 nm at its peak. Then the disinfected currency bills are diverted to stacker output receptacle 202. FIG. 14 illustrates that some disinfected currency bills 30b are sitting on the stacker output receptacle 202 after the process is completed in a matter less than a second and instantly and free of germs.

Figure 15:
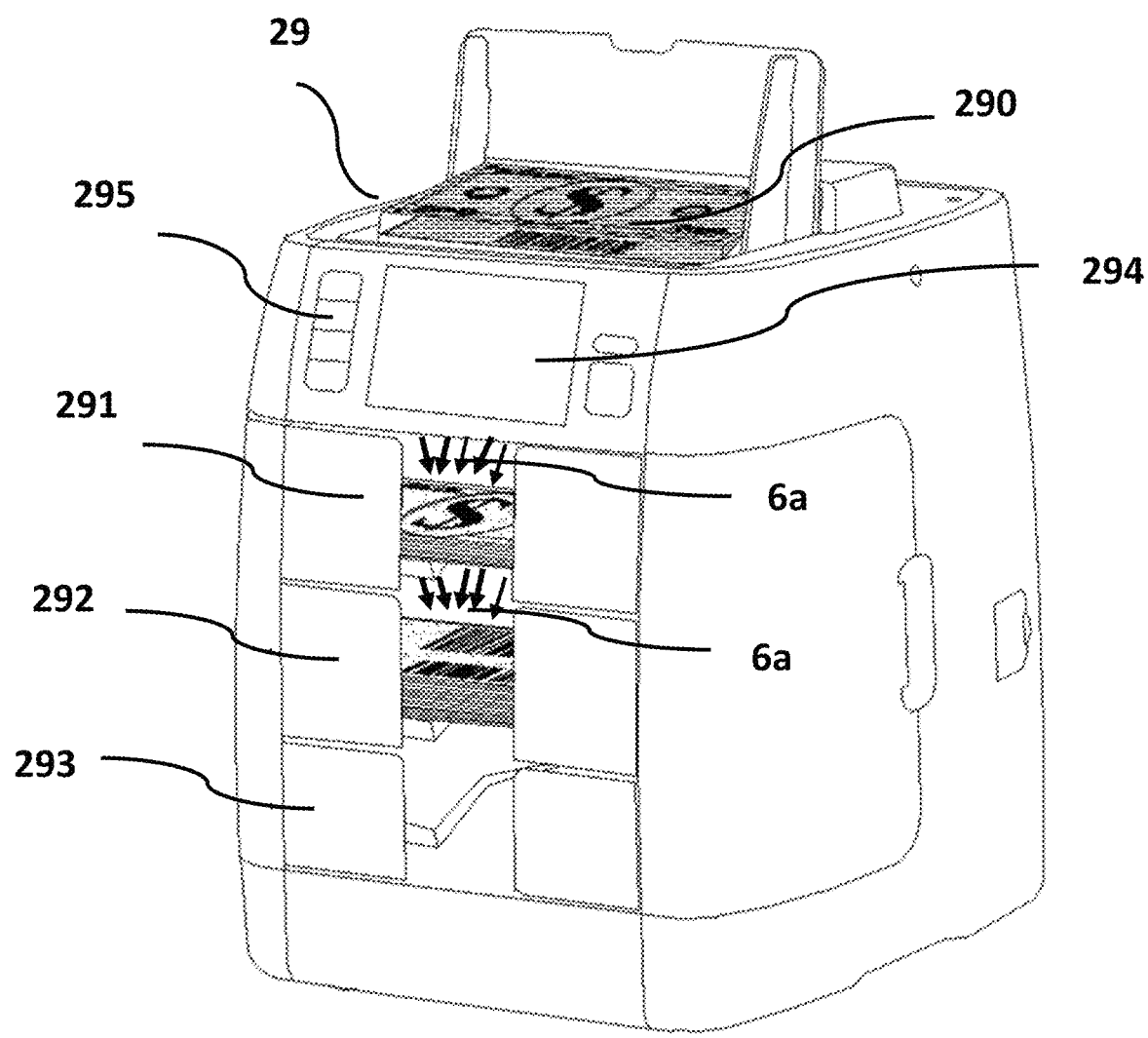
FIG. 15 is a perspective view of the currency bill processing device for denominating and sorting the currency bill and further shows UV-C irradiation of the currency bills, according to an exemplary embodiment of the present invention.
Figure 16:
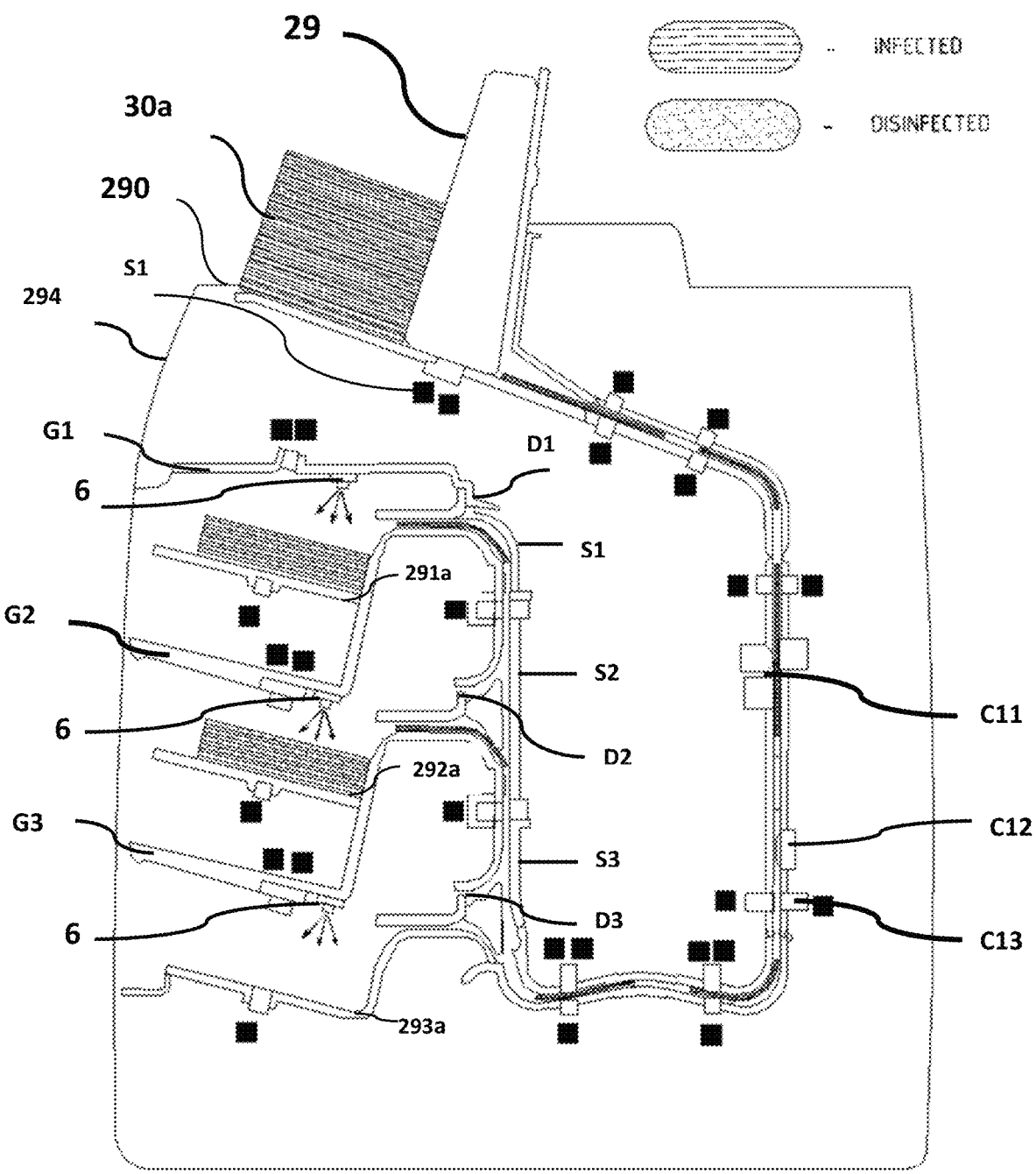
FIG. 16 is a cross-section view of the currency bill processing device shown in FIG. 15 further illustrating the components including the bill conveying path, currency recognition unit and authentication unit, two stacker output receptacles, one reject output receptacles, and the disinfection unit, according to an exemplary embodiment of the present invention.

Referring now to FIG. 15 showing currency bills processing device 29 and FIG. 16 shows an internal view of the currency bills processing device 29. The currency bills processing device 29 is structured, designed, and works under the same principle having similar functionality of the currency bills processing device 27 but having 2 stacker output receptacles 291 and 292 and one reject output receptacle 293. The currency bills processing device 29 is slightly larger in dimension compared to the currency bills processing device 27 and the currency bills processing device 28. The currency bills processing device 29 is about 12 inches in width, 13.2 inches in length, and 15 inches in height, still consider a compact currency denominating and sorting device in the cash processing industry.

The currency bills processing device 29 of FIG. 15 and FIG. 16, also includes a bill input station or receptacle or bill accepting station 290 where a stack of currency bills that need to be discriminated, recognized, and counted or currency media for which their barcode or MICR printed on them needed to be recognized and decoded, is placed. One skilled in the art of currency sorting device would understand that currency bills processing device 29 is a currency sorter and sorts of currency bills in separate stacker output receptacles and the user can place them together on the bill accepting station 290 in a mixture or separately for processing. Currency bills in a mixture or in separate, placed on the bill input receptacle 290 are acted upon by a bill sensor S1 (FIG. 16) to sense that there is an object placed on the bill input station and once sensed, bill and/or media than starts to feed and conveyed using of combination of feed rollers (not shown in FIG. 16) which is conventional in the art and a feed motor (not showing on the diagram and conventional in the art) one currency bill at a time with the narrow dimension of the bills being parallel to the bill input station 290 and currency recognition unit C11 (FIG. 16). Currency bills then pass the currency recognition unit C11 (FIG. 16) and several authentication units, such as ultraviolet light C13 (FIG. 16) and magneto-resistive (MR) sensor C12 (FIG. 16) where the currency bill is recognized, denomination of the bill is identified and discriminated, suspect detection checking is performed, and in case of currency media such as casino tickets, they are decoded for their printed barcode feature or reading of MICR (magnetic ink character recognition) in case of banknote check. It is well-known in the art that substitutes currency media are not subject to this authentication checking due to characteristics of currency media. Once judgment is made by the currency recognition unit C11 (FIG. 16) as to the type of denomination and value of the currency bills or currency media are properly recognized, read, and decoded, then currency bills are conveyed forward using of bill conveying mechanism at a speed up to 1000 bills per minute through bill conveying path S1, S2, S3 (FIG. 16) and drive upwards.

The currency bills conveying mechanism usually consists of many small rollers and shafts and the main motor (not show in the drawings and known in the art) to drive currency bills and/or currency media through currency bills conveying path S1, S2, S3 (FIG. 16) at a high-speed. The structure of such high-speed currency bills conveying mechanisms and motors are well-known in the art and so is not described herein in detail. The next step would be for conveying path, and motor to drive currency bills upwards and using driver D1, D2, and D3 (FIG. 16) found towards the end of conveying path for each receptacle and to divert currency bills to their respective stacker output receptacles or reject receptacles based on the judgment made by the currency recognition unit C11 and CPU. Each diverter is installed at the end of conveying path before currency bills enter the stacker output receptacles or reject the output receptacle. For example, D1 diverter diverts currency bills to Stacker output receptacle 291 or D2 diverter diverts currency bills to the stacker output receptacle 292. There is also a D3 diverter that diverts passing currency bills reject output receptacles and all these diversions are performed following the judgment made by the currency recognition unit C11 and CPU in conjunction with control panel 295 (FIG. 15) operation selected by users. Any currency bills not properly read or decoded are delivered to reject receptacle 293. Various counting modes, functions, such as batching, sorting, facing or orientation, or fitness is well-known in the art of currency processing, so, they are not described in detail here.

In accordance with the same principle and method that applied to the currency bills processing device 27 or the currency bills processing device 28 of FIG. 11, here is the currency bills processing device 29 of FIG. 15 and FIG. 16 is also having the UV-C LED strip 6. While currency bills processing device 27 only has one stacker output receptacle, here, currency bills processing device 29 of FIG. 15 and FIG. 16 has a plurality of output receptacles 291, 292 and reject receptacle 293 and installed with Stacker plates 291a and 292a which move up and down as currency bills are delivered there as well as reject plate 293a moves up and down as rejects bills are delivered there. Since these stackers plates 291a and 292b and reject receptacle plate 293a moves up and down, the elements of the embodiments of the present invention cannot be installed there as currency bills would come in direct contact with the elements of the present invention. Instead, the stacker plates 291a and 292a as well as reject output receptacle 293a also include a stacker guide bar plate G1 and G2 on both stackers on top of the stacker plate and G3 guide plate on top of reject receptacle 293a and they are fixed inside of the device 29. According to the present invention and method of placing the UV-C LED strip 6 in a compact area and facing the currency bills which are conveyed at a high-speed towards the output receptacles, so that UV-C radiation 6a would emit on them downwardly and irradiate and in the process, sterilize and disinfect them before currency bills are delivered to their end destination stackers. Even currency bills are not recognized or not read correctly by the currency recognition unit C11 and divert to reject output receptacle 293, on this device, those rejected currency bills 30a and currency media 31a will also be disinfected by the UV-C LED strip 6 installed on the outer side (opposite) of the reject output guide plate G3 (FIG. 16).

According to FIG. 16 illustration, the UV-C LED strip 6 is installed right after the diverter D1, D2, and D3 respectively as currency bills enter the output receptacle areas of 291, 292, and 293 and are installed underneath (outer side) the stacker guide bar plates G1, G2, and G3 having about 7.5 inches length facing the currency bills as they pass by towards the stacker output receptacles or reject output receptacle.

Figure 16A:
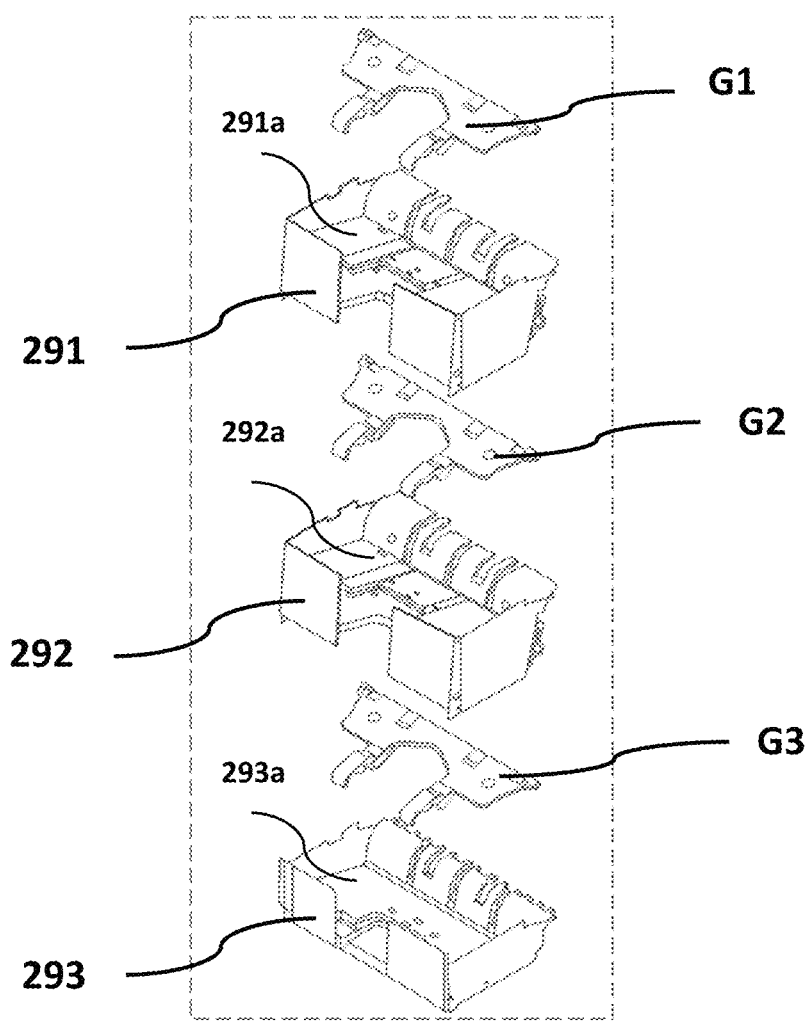
FIGS. 16a, 16b, and 16c show the stacker output receptacles and the reject output receptacle of the currency bill processing device shown in FIG. 15 further illustrating the stacker guide bar plate to which the UV-C strip is mounted on the outer side, according to an exemplary embodiment of the present invention.
Figure 16B:
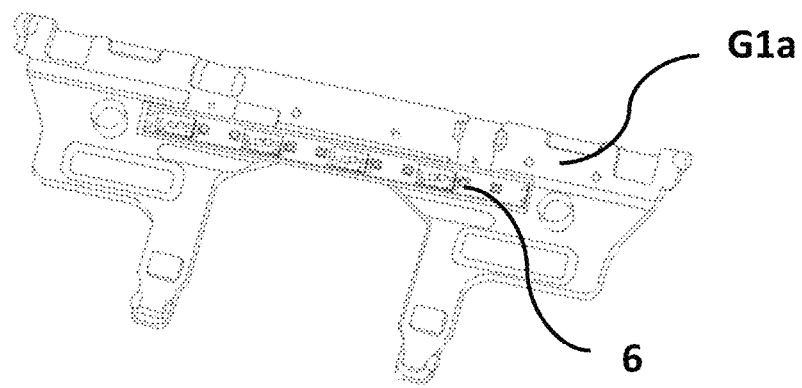
Figure 16C:
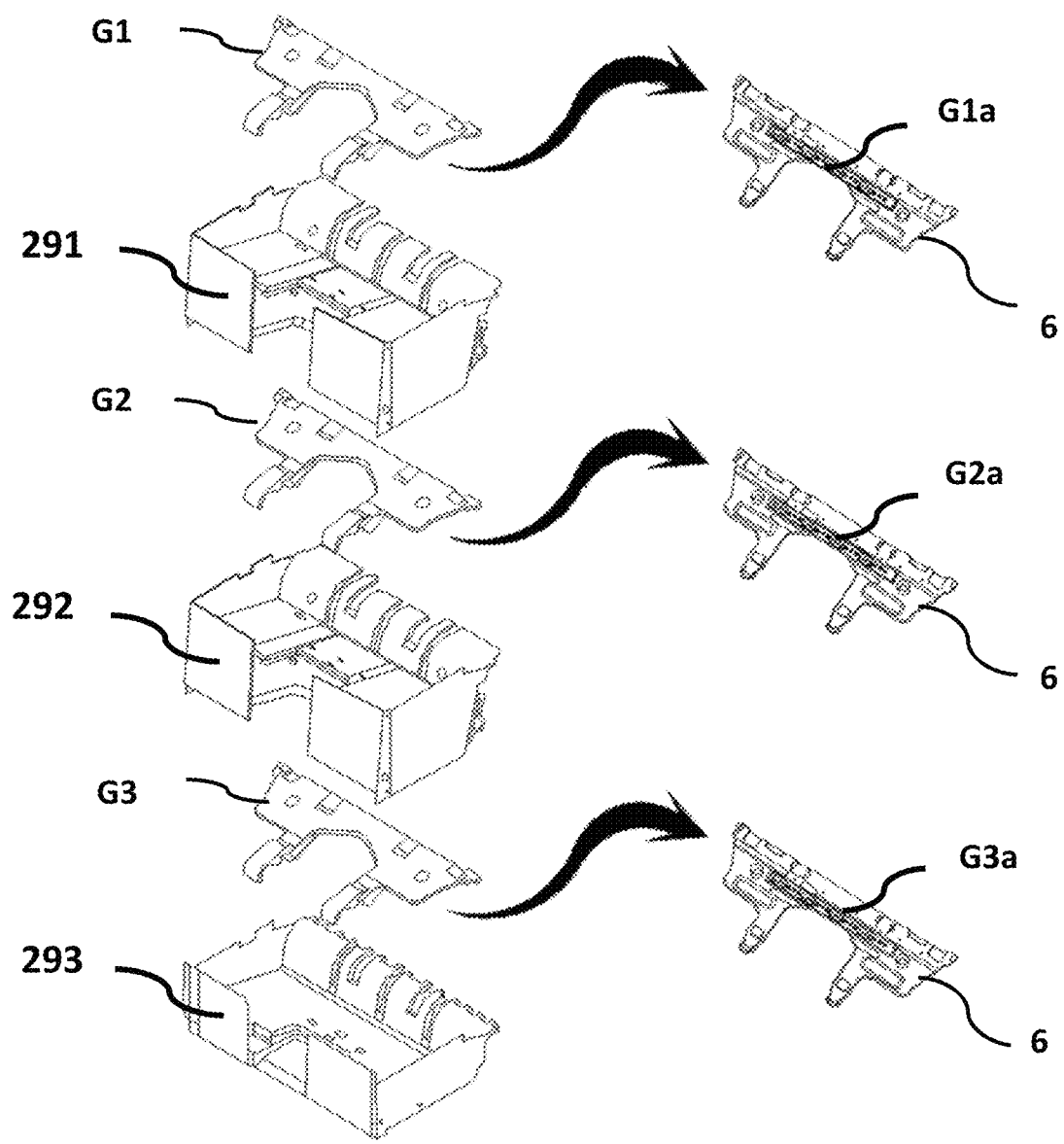

Referring now to FIGS. 16a, 16b, and 16c, they are perspective views of the stacker output receptacles 291 and 292 and reject output receptacle 293 of the currency bills processing device 29 of FIG. 16 and perspective view of stacker guide bar plate G1, G2, and G3 (FIG. 16) of the stacker output receptacles 291, 292 and reject output receptacle 293 of the device 29 of FIG. 15.

Referring again to FIG. 16b, it is a perspective rear view G1a of one of stacker guide bar plate G1 (FIG. 16) having about 7.5 inches in length having a rigid aluminum or copper base UV-C LED Strip 6. FIG. 16b illustrates the rearview G1a of one of the stacker guide bar plate G1 as an example because other stacker guide bar plates G2 and G3 (FIG. 16) having about 7.5 inches in length are the exact piece of hardware installed into the currency bills processing device 29 of FIG. 16. FIG. 16c further illustrates that 7" of a rigid aluminum or copper base UV-C LED strip 6, can conveniently fit into and mount onto the surface of the outer/rear side G1a of the stacker guide bar plate G1, outer/rear side G1a of the stacker guide bar plate G2, and outer/rear side G3a of the stacker guide bar plate G3 of currency bills processing device 29 effectively.

Figure 17:
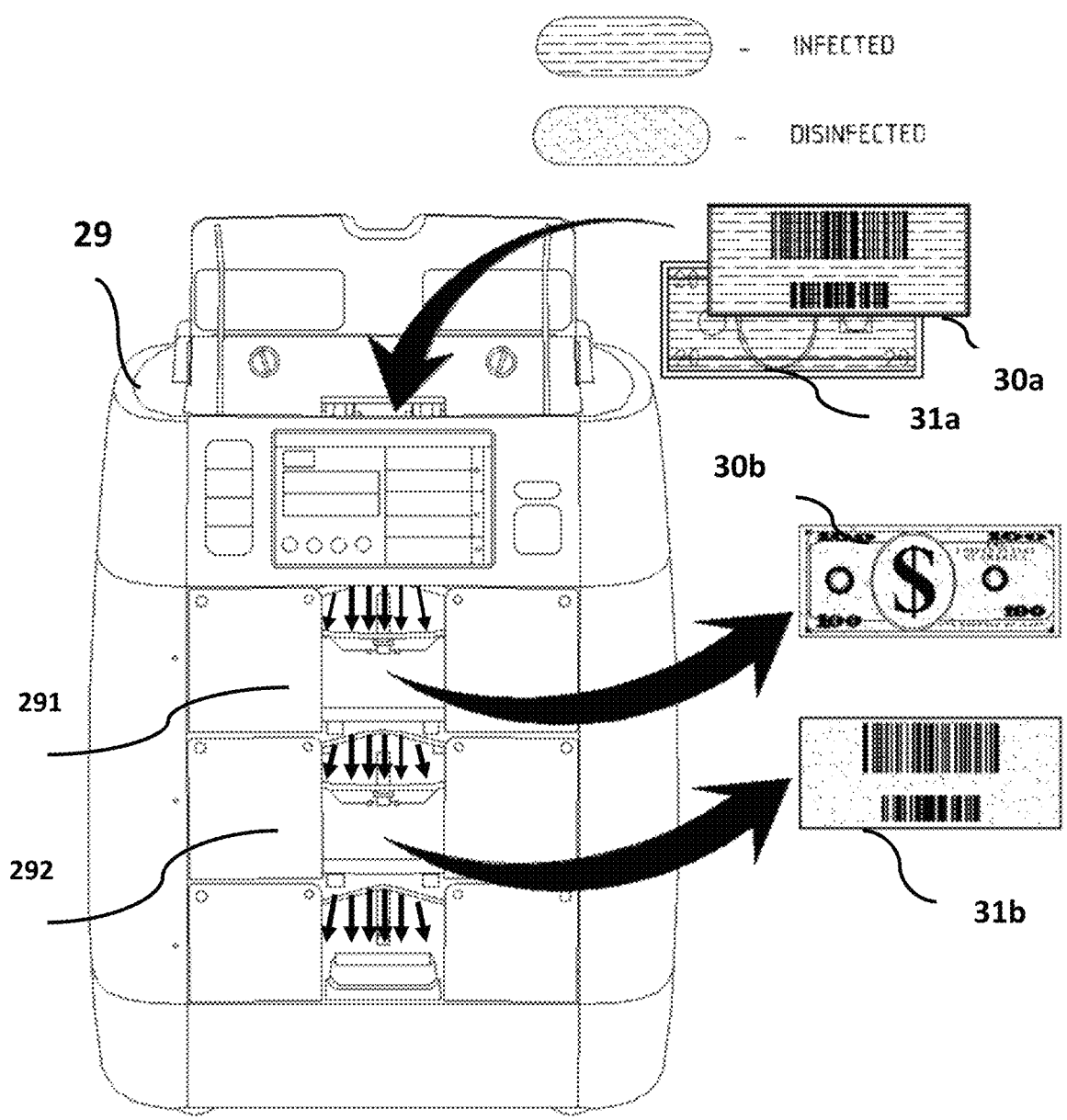
FIG. 17 shows the currency bill processing device as in FIG. 15 further illustrating the UV-C irradiation and disinfection of different currency bills, according to an exemplary embodiment of the present invention.

Referring now to FIG. 17, illustration is made showing infected currency bills 30a and substitutes currency media 31a, such as casino tickets placed in mixture on the bill input station 290 (FIG. 15) for processing and sorting to separate stacker output receptacles 291 and 292 and after they are recognized, discriminated, denominated and sorted determined by currency recognition unit C11 (FIG. 16) and CPU, then, diversion steps take place using of diverter as described above to deliver currency bills to stacker output receptacle 291 and currency media to 292 or reject receptacle 293 if they are not read correctly by C11 and CPU and once the currency bills and substitutes currency media enter into their respective stacker receptacles 291 and 292 entry path, and disinfected by the UV-C LED strip 6 at a frequency of about 269 nm at its peak. Even currency bills are not recognized or read correctly and divert to reject output receptacles, on this device, those will also be disinfected.

Figure 18:
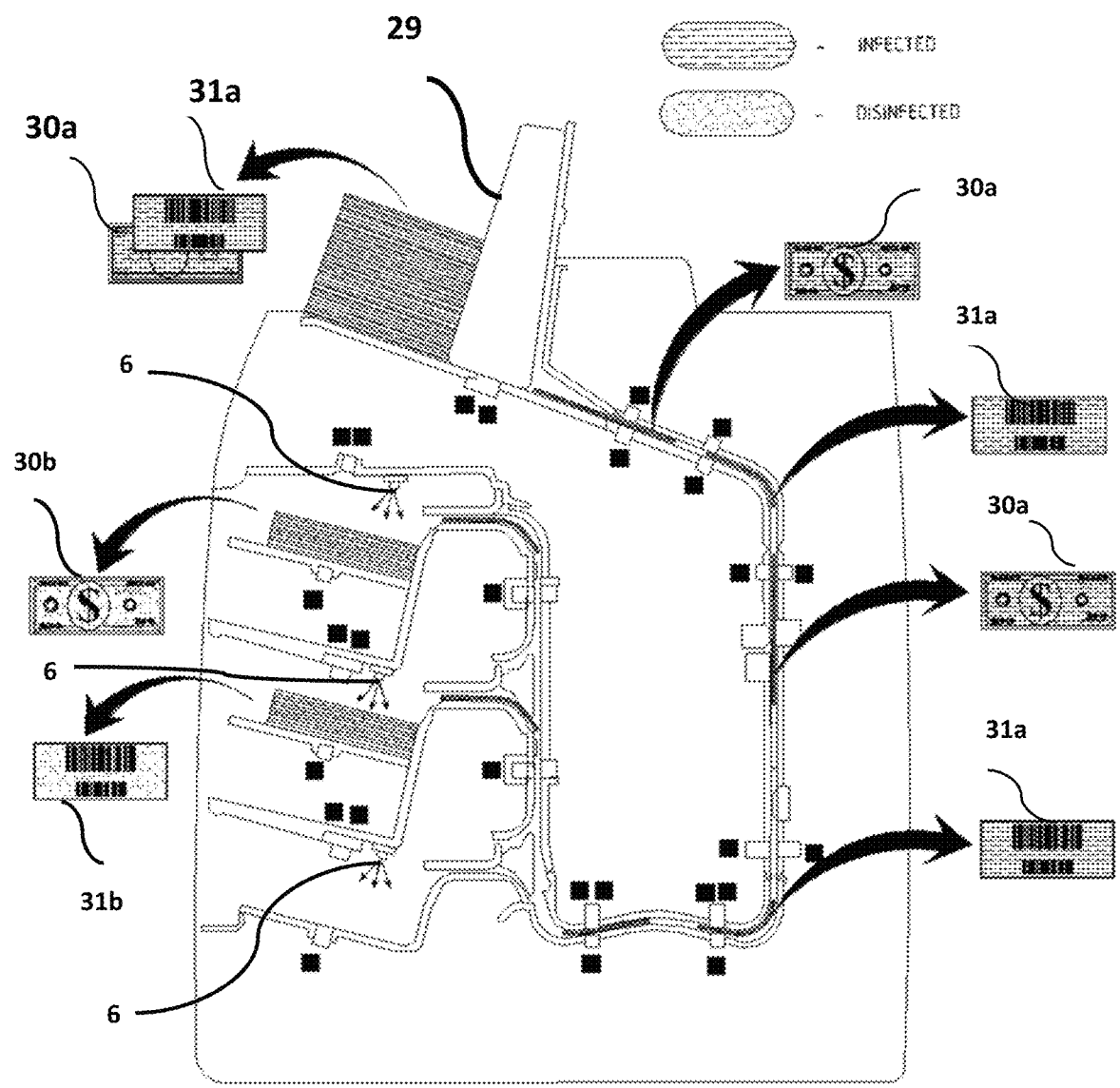
FIG. 18 shows the currency bill processing device as in FIG. 15 further illustrating sorting the infected currency bills, such as Casino tickets with the barcode into two separate stacker output receptacles after being disinfected by irradiating them with UV-C radiation, according to an exemplary embodiment of the present invention.

Referring FIG. 18, illustration is made showing infected currency bills 30a and substitutes currency media 31a, such as casino tickets placed in mixture on the bill input station 290 (FIG. 15), conveying infected currency bills 30a and currency media 31a at a high-speed through high-speed bill mechanism (not shown and known in the art) and trough the conveying path S1, S2, S3 (FIG. 16) and mechanism without being sterilized and disinfected by the elements of the embodiments of present invention and systems and after they are recognized, discriminated, denominated and sorted determined by currency recognition unit C11 (FIG. 16) and CPU, then, diversion steps take place using of diverter as described above to deliver currency bills to stacker output receptacle 291 and currency media to 292 or reject receptacle 293 if they are not read correctly by C11 and CPU and once the currency bills and currency media enter into their respective stacker receptacles 291 and 292 entry path, currency bills and currency media then finally disinfected at a frequency of about 269 nm at its peak (FIG. 7c), prior they are deliver to their respective stacker output receptacles 291 for currency bills. Even currency bills are not recognized or read correctly and divert to reject output receptacles, on this device, will also be disinfected. This entire disinfection process is done for hundreds of currency bills and/or media in a matter of few seconds and instantly before anyone gets to touch the currency bills on the device and when they do, they will then be in possession of currency bills free of germs.

Figure 19:
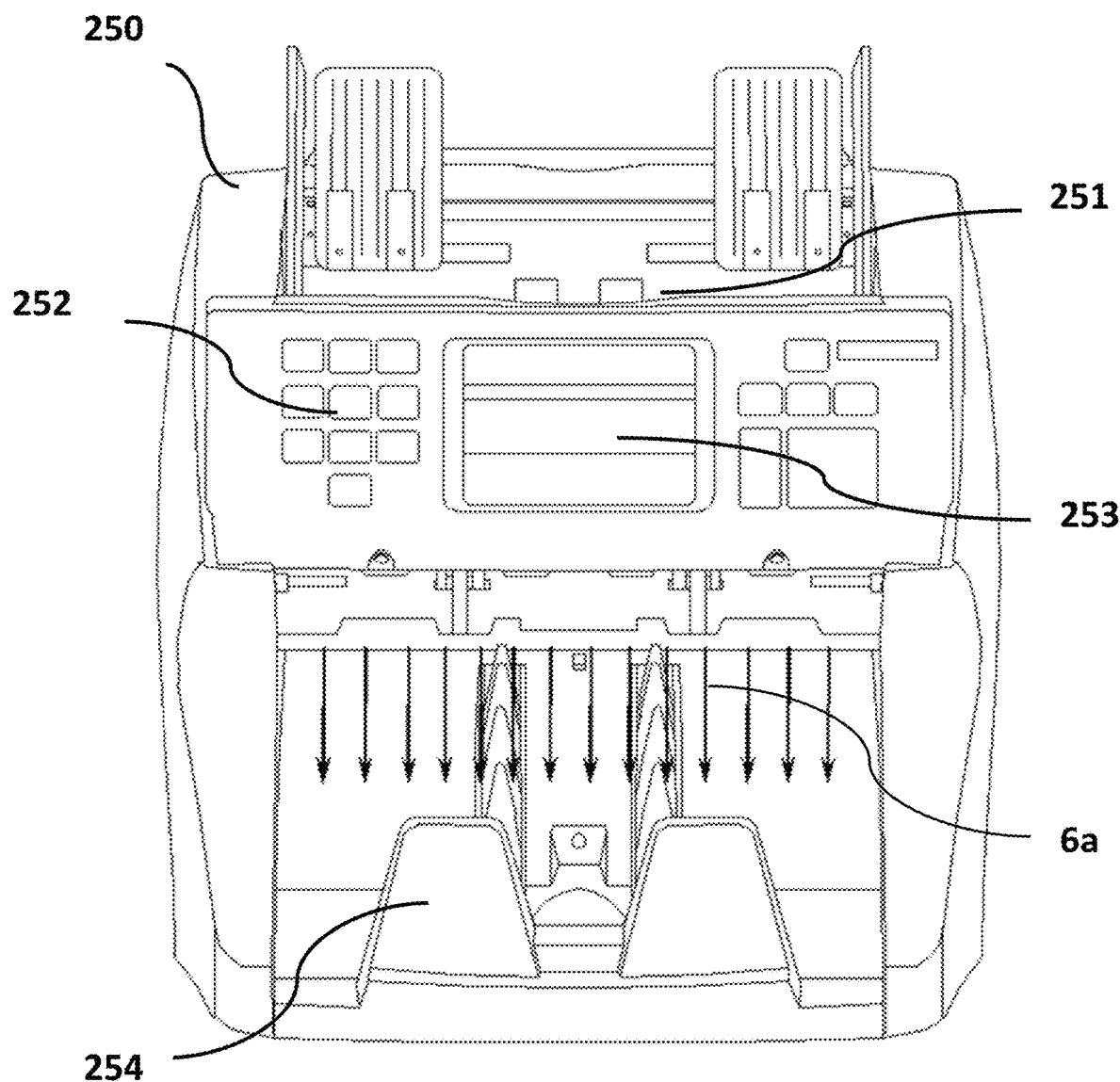
FIG. 19 is a perspective view of another exemplary embodiment of the currency bill processing device having one output receptacle, according to an exemplary embodiment of the present invention.
Figure 22:
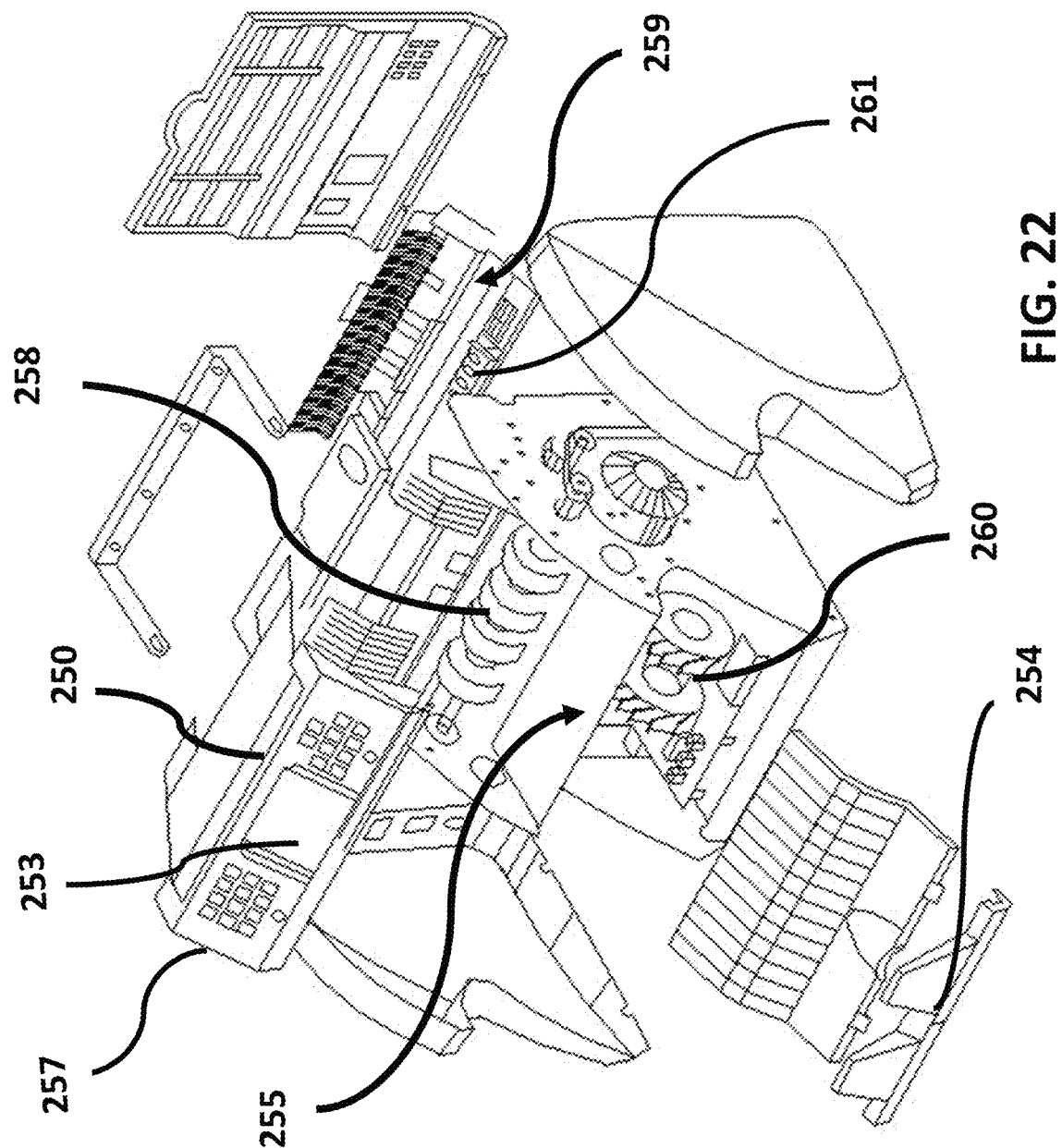
FIG. 22 is an exploded view of the currency bill processing device shown in FIG. 19, according to an exemplary embodiment of the present invention.

Referring now to FIG. 19 and FIG. 22 together, there are shown a perspective view of currency bills processing device 250, and FIG. 22 is a complete break-down of currency bill processing device 250 illustrates the location of the support plate 255 where the UV-C LED strip 6 is installed. Again, referring to FIG. 19, the currency bills processing device 250 has only one output receptacle 254 and dimension of about 11" width, 10.3" length, and 10.6" height, even compact size compares the currency bills processing device 27 and). The currency denominating device 250 includes a bill input station or receptacle or bill accepting station 251 where a stack of currency bills to be discriminated, recognized, and counted is placed. Currency bills in the bill input receptacle 251 are acted upon by a bill sensor (not shown) to sense that there is an object placed on the bill input station 251 and once sensed, the bill then starts to feed and conveyed using of combination of feed rollers 258 (FIG. 22) and feed motor 260 (FIG. 22) which are typical and known in the art, one bill at a time with the narrow dimension of the bills being parallel to the bill input station 251. Currency bills then pass an optical currency recognition unit 259 (FIG. 22) which is conventional and known in the art and several typical authentication units, such as ultraviolet light and magneto-resistive (MR) sensor 261 (FIG. 22) and utilizing all these recognition and authentication units, the currency bill is recognized, denomination of the bill is identified and discriminated, suspect detection checking is performed by the device 250 of FIG. 18, FIG. 19). Once judgment is made by the optical currency recognition unit 259 (FIG. 22) as to the currency type, denomination, and value of the currency bills or decodes the barcode printed on a casino ticket or MICR printed on a banknote, then currency bills or currency media then conveyed forward using of bill conveying mechanism (not shown) at a speed up to 1000 to 1200 pcs per minute via typical short bill conveying path (not shown) passing a support plate 255 located underneath of display control panel unit 257 (FIG. 22) and then, deliver to the only output/stacker output receptacle 254 using of stacker wheels 256 (FIG. 20) for proper alignment.

One skilled in the art of currency processing devices would understand that currency denominating device 250 include a CPU on the mainboard, which is programmed to determine the country of bills, count the number of currency bills, denomination of each recognized currency bill, and determine the cumulative total of the currency amount represented by the currency bills scanned through optical currency recognition unit 259 (FIG. 22). The CPU is also linked to a control panel 257 (FIG. 20) consisting of buttons or keypad 252 (FIG. 22) for selection of various functionality and operation of the device and include an LCD display unit 253 (FIG. 22) which is adapted to provide a display of the number of bills counted, the breakdown of the bills and currency denomination, and the cumulative total of the currency value represented by counted bills. The display unit 253 (FIG. 19) can also be adapted to provide a print-out of the displayed information in the desired format if an external printer device is connected to CPU and CPU is also connected to RS232 interface ports usually located at the rear side of the device to connect to printer and external display unit which are typical (not shown here) to show the count and break-down of count as it displayed.

Figure 20:
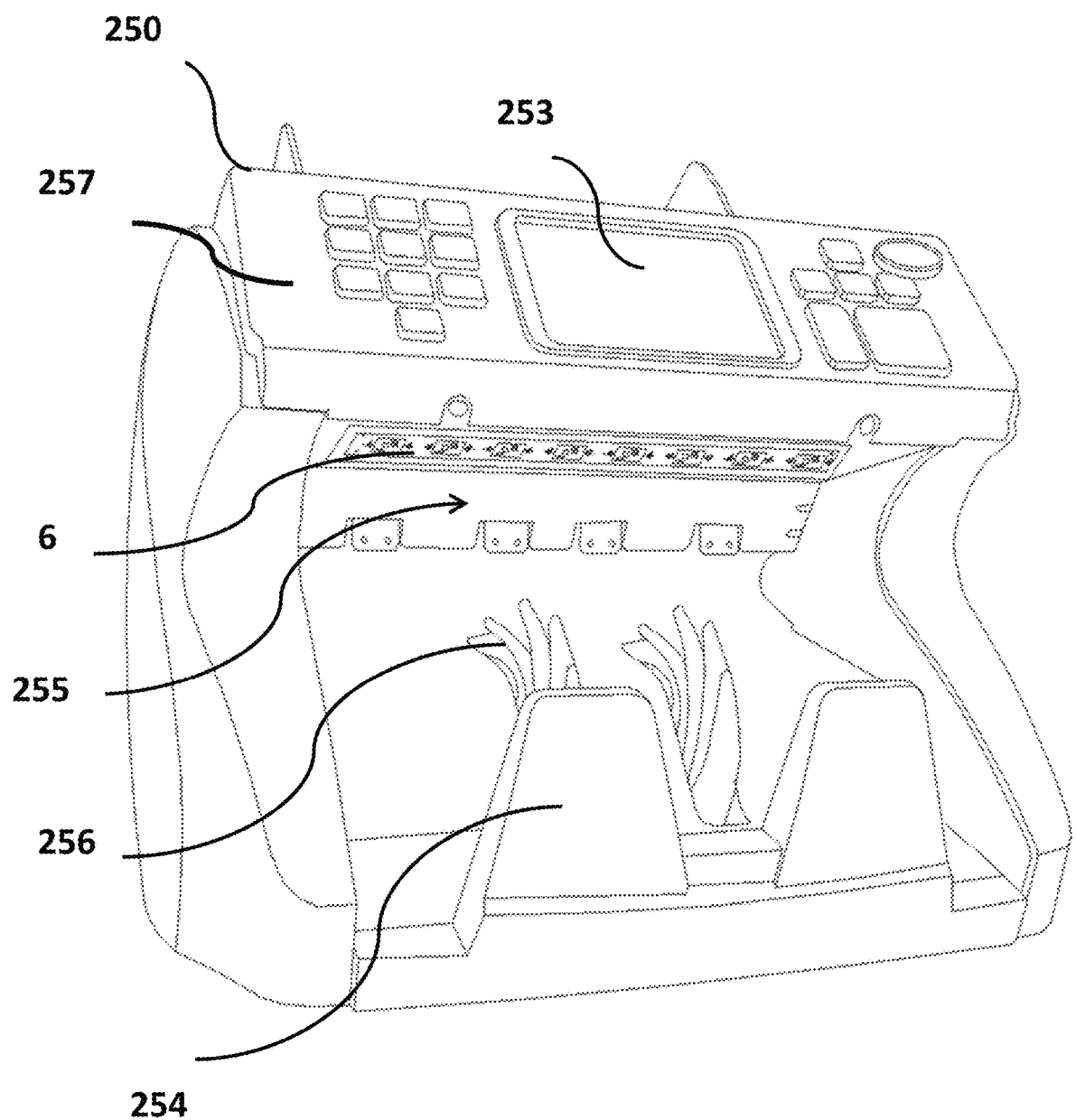
FIG. 20 is another perspective view of the currency bill processing device, according to an exemplary embodiment of the present invention.

Referring to FIG. 20, which shows the UV-C LED strip 6 is conveniently installed on outer side/underneath of a support plate 255 (FIG. 22) having about 7.5" length with about 4" width of open area which is located below the control panel 257 and above the only stacker output receptacle 254 of this alternative device 250 of FIG. 19. FIG. 20 illustrates that this support plate 255 is a part of the control panel assembly 257 having no moving parts and fixed with other parts of the control panel assembly 257 and when currency bills pass through outer side/underneath of this support plate 255 (FIG. 21), the UV-C LED strip 6 emit UV-C radiation 6a (FIG. 19) on the passing currency bills downwardly from the plate 255 location area and in the process, disinfect currency bills before they are delivered to the only stacker output receptacle 254 and ready for users to remove the sterilized and disinfected currency bills for further processing or handing out to customers.

Figure 20A:
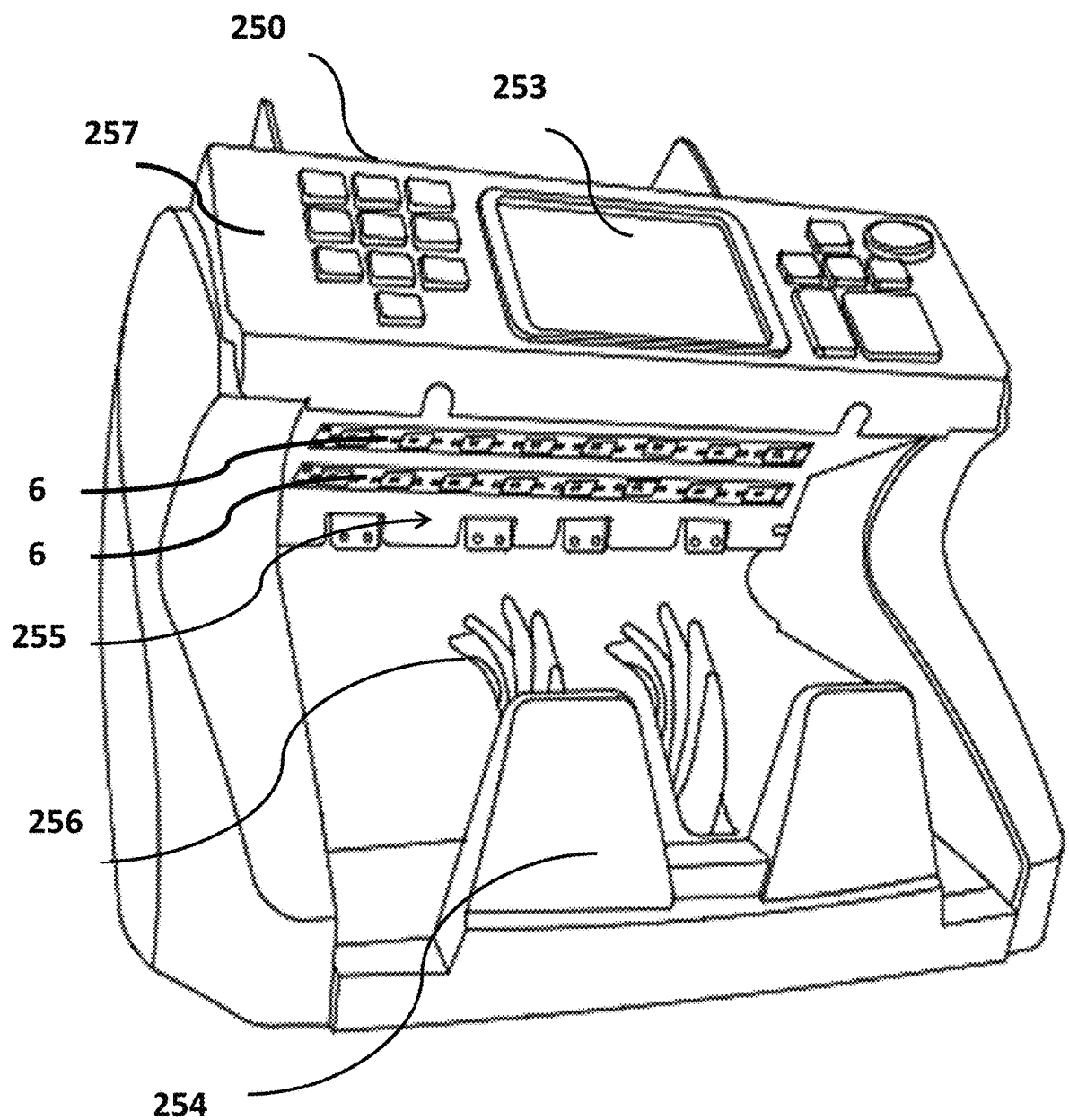
FIG. 20a shows the currency bill processing device as in FIG. 19 having two units of the UV-C LED strips installed underneath (outer side) a support plate, according to an exemplary embodiment of the present invention.

Referring to FIG. 20a, illustrates the currency bills processing device 250 has two UV-C LED strip 6, conveniently installed on the outer side/underneath of a support plate 255 (FIG. 22) having about 7.5" length with about 4" width of open area which is located below the control panel 257 and above the only stacker output receptacle 254 of currency bill processing device 250. FIG. 20a illustrates the support plate 255 where two UV-C LED strip 6 are installed, is a part of the control panel assembly 257 having no moving parts and fixed with other parts of the control panel assembly 257 and when currency bills pass underneath of this support plate 255 (FIG. 21), the installed two UV-C strip 6 emit UV-C radiation 6a on the passing currency bills downwardly from the plate 255 location area and in the process, disinfect currency bills before they are delivered to the only stacker output receptacle 254 and ready for users to remove the sterilized and disinfected currency bills for further processing or handing out to customers.

Figure 21:
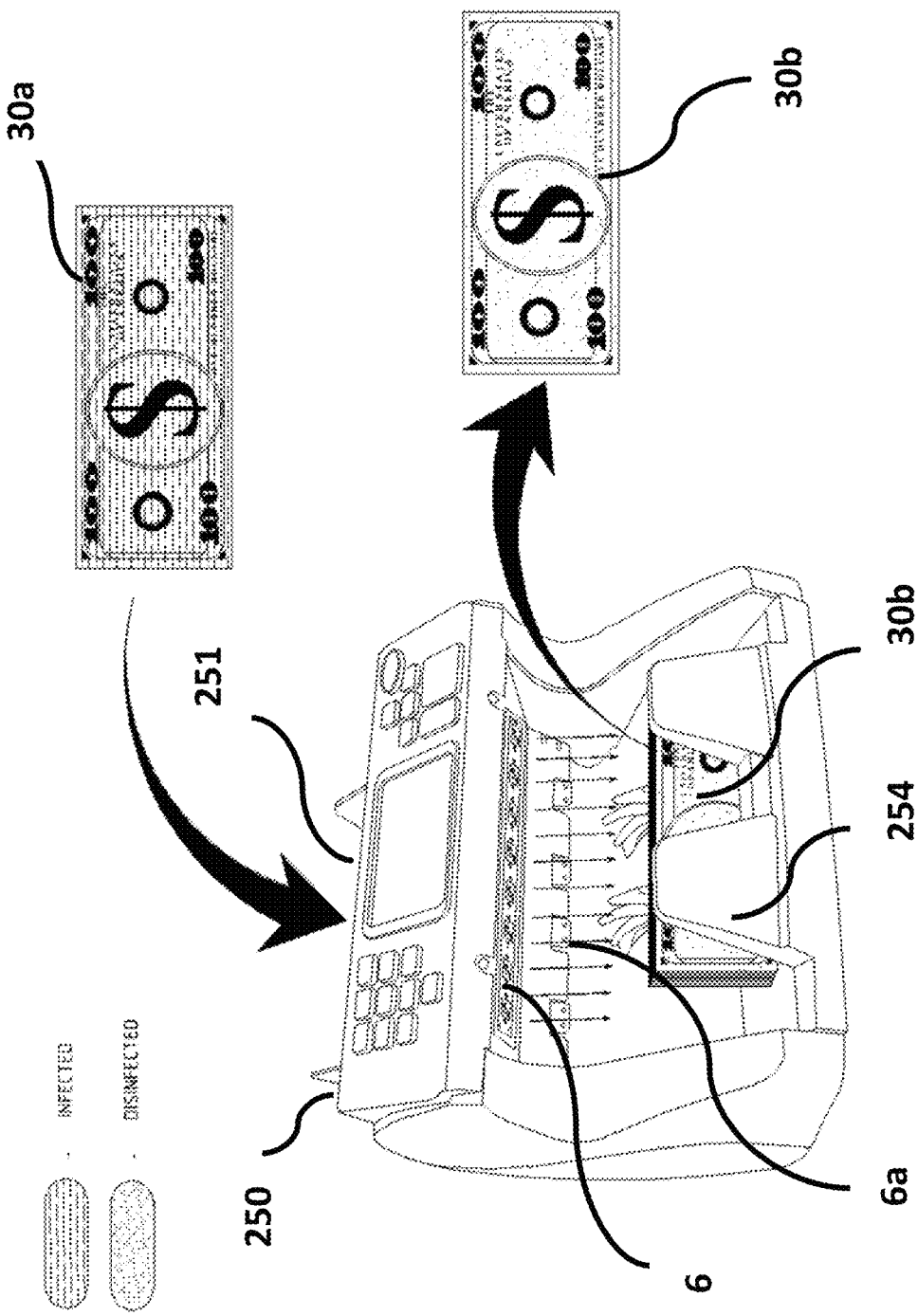
FIG. 21 is a perspective view of the currency bill processing device as in FIG. 19 further illustrating the passing of infected currency bills and UV-C irradiation of the infected currency bills, according to an exemplary embodiment of the present invention.

Referring to FIG. 21, it is a perspective view of the currency bill processing device 250 further illustrating infected currency bills 30a on the bill input station 251 and after they are disinfected by the UV-C LED strip 6, then conveyed and deliver to the only stacker output receptacle 254. FIG. 21 shows currency bills 30b passing under the UV-C LED strip 6 at close proximity of about 1 cm distance far apart and at a high-speed of up to 1000 bills per minute and irradiated by UV-C rays or radiation 6a at a frequency of about 269 nm at its peak, are disinfected and sitting on the stacker output receptacle 254 free of germs, so that they can be handed to customers by bank tellers or clerks of the cash register at various retail outlets, restaurant-bar-nightclubs, casinos and gaming among other places use cash as the primary source of exchange.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A currency bill processing device comprising:
   a bill input station for receiving currency bills;
   at least one output stacking receptacle;
   a currency bill conveying mechanism configured to convey the currency bills from the bill input station to the at least one output stacking receptacle;
   a currency bill recognition unit configured to count and/or discriminate the currency bills, the currency bill recognition unit operably coupled to the currency bill conveying mechanism;
   a disinfecting unit comprising at least one elongated UV-C LED strip, the at least one elongated UV-C LED strip is configured to irradiate the currency bills for disinfecting the currency bills; and
   a reject output receptacle, the reject output receptacle has a plate, the plate has an inner surface and an outer surface, the reject output receptacle operably coupled to the currency bill conveying mechanism, the reject output receptacle is configured to receive one or more of the currency bills on the inner surface, and wherein the at least one elongated UV-C LED strip is positioned on the outer surface of the plate of the reject output receptacle.

2. The currency bill processing device according to claim 1, wherein the disinfecting unit further comprises a rigid base made of copper or aluminum, the at least one elongated UV-C LED strip is mounted to the rigid base, and the rigid base is mounted to the outer surface of the reject output receptacle.

3. The currency bill processing device according to claim 2, wherein a length of the at least one elongated UV-C LED strip is equal to or more than a length of a currency bill of the currency bills.

4. The currency bill processing device according to claim 3, wherein the at least one elongated UV-C LED strip is about 7 inches in length and about 0.5 inches in width, the at least one elongated UV-C LED strip has at least eight UV LEDs arranged linearly along the length of the at least one elongated UV-C LED strip, and wherein the eight UV LEDs are configured to emit UV radiation in a wavelength range of about 260-280 nm.

5. The currency bill processing device according to claim 3, wherein a length of the rigid base is about 7.5 inches.

6. The currency bill processing device according to claim 2, wherein a closest distance between the currency bills and the at least one elongated UV-C LED strip is about 1 cm.

7. The currency bill processing device according to claim 2, wherein the disinfecting unit further comprises a relay, the relay operably coupled to both the currency bill conveying mechanism and the at least one elongated UV-C LED strip, the currency bill conveying mechanism comprises a motor, the relay is configured to energize and de-energize with activation and deactivation of the currency bill conveying mechanism respectively, wherein the energizing of the relay turns on the at least one elongated UV-C LED strip and the de-energizing of the relay turns off the at least one elongated UV-C LED strip.

8. The currency bill processing device according to claim 1, wherein the at least one elongated UV-C LED strip is adjacent to the at least one output stacking receptacle.

9. The currency bill processing device according to claim 8, wherein the at least one elongated UV-C LED strip is positioned to emit radiation downwards and rearwardly over the currency bills and the radiation does not either directly or by reflection reach out of the currency bill processing device.

10. The currency bill processing device according to claim 4, wherein the at least one elongated UV-C LED strip comprises two elongated UV-C LED strips mounted parallel to each other on the rigid base.

11. The currency bill processing device according to claim 1, wherein the currency bill processing device further comprises a power supply, the power supply electrically coupled to the currency bill conveying mechanism, wherein the disinfecting unit further comprises a voltage converter, the voltage converter electrically coupled to the power supply.

12. The currency bill processing device according to claim 1, wherein the currency bill processing device further comprises a power supply, the power supply electrically coupled to the currency bill conveying mechanism and the disinfecting unit.

13. The currency bill processing device according to claim 1, wherein the currency bill conveying mechanism is configured to convey the currency bills at a rate of about 1000 currency bills per minute, and wherein the disinfecting unit is configured to disinfect the currency bills at the same rate.

14. A currency bill processing device comprising:
a bill input station for receiving currency bills;
at least one output stacking receptacle, wherein the at least one output stacking receptacle comprises two or more output stacking receptacles, each of the two or more output stacking receptacles has a bottom plate, the bottom plate has an inner surface and an outer surface, the two or more output stacking receptacles arranged one above another such that the outer surface of the bottom plate of an output stacking receptacle of the two or more output stacking receptacles faces the inner surface of the bottom plate of an adjacent output stacking receptacle of the two or more output stacking receptacles;
a currency bill conveying mechanism configured to convey the currency bills from the bill input station to the two or more stacking receptacles;
a currency bill recognition unit configured to count and/or discriminate the currency bills, the currency bill recognition unit operably coupled to the currency bill conveying mechanism; and
one or more UV-C LED strips are coupled to the outer surface of the bottom plate of one or more output stacking receptacles of the two or more output stacking receptacles.

15. The currency bill processing device according to claim 14, wherein the currency bill processing device further comprises a top plate positioned above a top output stacking receptacle of the two or more output stacking receptacles, wherein the top plate has the one or more UV-C LED strips on a bottom surface of the top plate.

16. A method for counting and/or discriminating currency bills and disinfecting currency notes, the method comprising the steps of:

providing a currency bill processing device comprising:
a bill input station for receiving currency bills,
at least one output stacking receptacle,
a currency bill conveying mechanism comprising a plurality of rollers configured to convey the currency bills from the bill input station to the at least one output stacking receptacle,
a stacker wheel configured to stack the currency bills into the at least one output stacking receptacle,
a currency bill recognition unit configured to count and/or discriminate the currency bills, the currency bill recognition unit operably coupled to the currency bill conveying mechanism, and
a disinfecting unit positioned adjacent to both the stacker wheel and the at least one output stacking receptacle, the disinfecting unit comprising a rigid base and at least one elongated UV-C LED strip, the at least one elongated UV-C LED strip is mounted to the rigid base, the rigid base is mounted spatially above the stacker wheel, the at least one elongated UV-C LED strip is configured to irradiate the currency bills adjacent to the stacker wheel for disinfecting the currency bills;
conveying the currency bills one at a time by the currency bill conveying mechanism for counting and/or discriminating by the currency bill recognition unit; and
upon counting and/or discriminating, irradiating the currency bills using the disinfecting unit.

17. The method according to claim 16, wherein the method further comprises the steps of:
upon irradiating, receiving the currency bills in the at least one output stacking receptacle.

18. The method according to claim 16, wherein a length of the at least one elongated UV-C LED strip is equal to or more than a length of a currency bill of the currency bills and wherein the at least one elongated UV-C LED strip comprises two elongated UV-C LED strips mounted parallel to each other on the rigid base.

19. The method according to claim 16, wherein the disinfecting unit further comprises a relay, the relay operably coupled to both the currency bill conveying mechanism and the at least one elongated UV-C LED strip, the currency bill conveying mechanism further comprises a motor, the relay configured to energize and de-energize with activation and deactivation of the currency bill conveying mechanism respectively, wherein the energizing of the relay turns on the at least one elongated UV-C LED strip and the de-energizing of the relay turns off the at least one elongated UV-C LED strip.

20. The method according to claim 16, wherein the at least one elongated UV-C LED strip is positioned to emit radiation downwards and rearwardly over the currency bills and the radiation does not either directly or by reflection reach out of the currency bill processing device.

* * * * *